US 6,929,909 B2

(12) United States Patent
Siebel et al.

(10) Patent No.: US 6,929,909 B2
(45) Date of Patent: Aug. 16, 2005

(54) GENE TARGETING VECTORS COMPRISING CONDITIONAL POSITIVE SELECTION MARKERS

(75) Inventors: Christian Siebel, Berkeley, CA (US); Thomas J. Brennan, South San Francisco, CA (US)

(73) Assignee: Deltagen, Inc., San Carlos, CA (US)

( * ) Notice: Subject to any disclaimer, the term of this patent is extended or adjusted under 35 U.S.C. 154(b) by 59 days.

(21) Appl. No.: 09/954,483

(22) Filed: Sep. 17, 2001

(65) Prior Publication Data

US 2003/0032175 A1 Feb. 13, 2003

Related U.S. Application Data

(60) Provisional application No. 60/232,957, filed on Sep. 15, 2000.

(51) Int. Cl.$^7$ .......................... C12Q 1/68; C12N 15/11; C12N 15/09; C12N 15/00; C07H 21/04

(52) U.S. Cl. .......................... 435/6; 435/91.4; 435/455; 435/440; 435/325; 435/69.1; 435/29; 435/320.1; 536/23.1

(58) Field of Search ................................ 435/914, 440, 435/455, 325, 6, 29, 320.1, 69.1; 536/23.1

(56) References Cited

U.S. PATENT DOCUMENTS

| 5,530,178 A | 6/1996 | Mak |
| 5,625,122 A | 4/1997 | Mak |
| 5,627,059 A | * 5/1997 | Capecchi et al. ............. 800/21 |

FOREIGN PATENT DOCUMENTS

| WO | WO 93/16177 | 8/1993 |
| WO | WO 94/29442 | 12/1994 |
| WO | WO 99/20780 | 4/1999 |

OTHER PUBLICATIONS

Kuebler, et al. "Functional Analysis of the DNA–Packaging/Terminase Protein gp17 from Bacteriophage T4", Journal of Molecular Biology, vol. 281, pp. 803–814, 1998.*

A. Bradley et al., "Site–Directed Mutagenesis in the Mouse," Recent Progress in Hormone Research, vol. 48, 1993, pp. 237–251.

J. Snouwaert et al., "An Animal Model for Cystic Fibrosis Made by Gene Targeting," Science, vol. 257, Aug. 21, 1992, pp. 1083–1088.

J. Dorin et al., "Cystic Fibrosis in the Mouse by Targeted Insertional Mutagenesis," Nature, vol. 359, Sep. 17, 1992, pp. 211–215.

A. Silva et al., "Deficient Hippocampal Long–Term Potentiation in α–Calcium–Calmodulin Kinase II Mutant Mice," Science, vol. 257, Jul. 10, 1992, pp. 201–206.

C. M. Knudson et al., "Bax–Deficient Mice With Lymphoid Hyperplasia and Male Germ Cell Death," Science, vol. 270, Oct. 6, 1995, pp. 96–99.

N. Wang et al., "Impaired Energy Homeostasis in C/EBPα Knockout Mice," Science, vol. 269, Aug. 25, 1995.

K. Paigen, "A Miracle Enough: the Power of Mice," Nature Medicine, vol. 1, No. 3, Mar. 1995, pp. 215–220.

R. Bollag et al., "Homologous Recombination in Mammalian Cells," Annu. Rev. Genet., vol. 23, 1989, pp. 199–225.

(Continued)

Primary Examiner—Gerry Leffers
(74) Attorney, Agent, or Firm—John E. Burke; Greenberg Traurig LLP

(57) ABSTRACT

The present invention is directed to methods and compositions useful in producing cells and animals having a disruption or modification of a target gene. Vectors useful in producing these cells and animals are described. In addition, methods of screening and enriching cells comprising a targeted gene modification are provided.

27 Claims, 16 Drawing Sheets

OTHER PUBLICATIONS

R. Kucherlapati et al., "Homologous Recombination Between Plasmids in Mammalian Cells can be Enchanced by Treatment of Input DNA," Proc. Natl. Acad. Sci., vol. 81, May 1984, pp. 3153–3157.

T. Doetschman et al., "Targetted Correction of a Mutant HPRT Gene in Mouse Embryonic Stem Cells," Nature, vol. 330, No. 10, Dec. 10, 1987, pp. 576–578.

O. Smithies et al., "Insertion of DNA Sequences Into the Human Chromosomal β–Globin Locus by Homologous Recombination," Nature, vol. 317, Sep. 19, 1985, pp. 230–234.

K. Song et al., "Accurate Modificaition of a Chromosomal Plasmid by Homologous Recombination in Human Cells," Proc. Natl. Acad. Sci., vol. 84, Oct. 1987, pp. 6820–6824.

H. Kim et al., "Recombinant Fragment Assay for Gene Targetting Based on the Polymerase Chain Reaction," Gene, vol. 16, No. 18, Aug. 1988, pp. 8887–8903.

E. Shesely et al., "Correction of a Human βs–Globin Gene by Gene Targeting, " Proc. Natl. Acad. Sci., vol. 88, May 1991, pp. 4294–4298.

H. Kim et al., "Problems Encountered in Detecting a Targeted Gene by the Polymerase Chain Reaction," Gene, vol. 103, May 1991, pp. 227–233.

M. Capecchi, "The New Mouse Genetics: Altering the Genome by Gene Targeting," Trends in Genetics, vol. 5, No. 3, Mar. 1989, pp. 70–77.

M. Capecchi, "Altering the Genome by Homologous Recombination," Science, vol. 244, No. 4910, Jun. 16, 1989, pp. 1288–1292.

Y. Yanagawa et al., "Enrichment and Efficient Screening of ES Cells Containing a Targeted Mutation: the use of DT–A Gene With the Polyadenylation Signal as a Negative Selection Maker," Transgenic Research, vol. 8, Feb. 1999, pp. 215–221.

M. Hu et al., "A Combination of Derepression of the *lac* Operator–Repressor System With Positive Induction by Glucocorticoid and Metal Ions Provides a High–Level–Inducible Gene Expression System Based on the Human Metallothionein–IIA Promoter," Molecular and Cellular Biology, vol. 10, No. 12, Dec. 1990, pp. 6141–6151.

M. Hu et al., "The Inducible *lac* Operator–Repressor System is Functional for Control of Expression of Injected DNA in Xenopus Oocytes," Gene, vol. 62, 1988, pp. 301–313.

M. Hu et al., "The Inducible *lac* Operator–Repressor System is Functional in Mammalian Cells," Cell, vol. 48, Feb. 27, 1987 pp. 555–566.

M. Hu et al., "Targeting the *Escherichia coli lac* Repressor to the Mammalian Cell Nucleus," Gene, vol. 99, 1991, pp. 141–150.

G. Hannan et al., "An Engineered PGK Promoter and *lac* Operator–Repressor System for the Regulation of Gene Expression in Mammalian Cells," Gene, vol. 130, 1993, pp. 233–239.

* cited by examiner

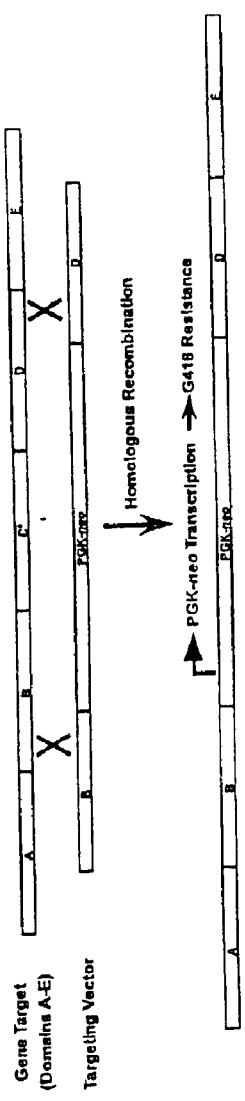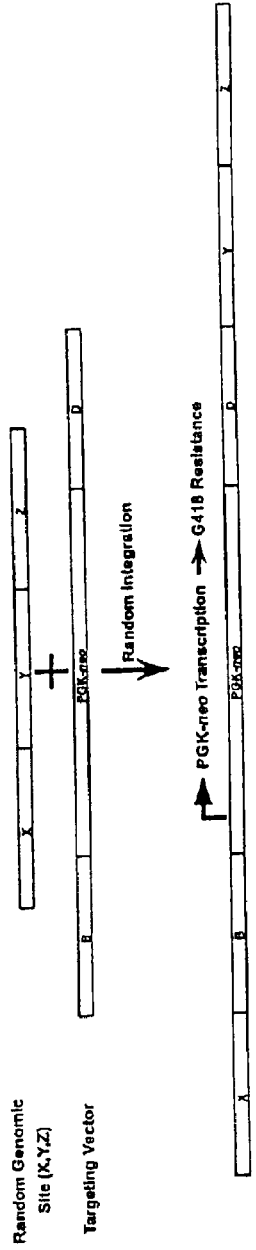
FIGURE 2

C14061:

```
GTTAACTACGTCAGGTGGCACTTTTCGGGGAAATGTGCGCGGAACCCCTATTTGTTTATTTTTCTAAATACATTCAAATATGTATCCGC
TCATGAGACAATAACCCTGATAAATGCTTCAATAATATTGAAAAAGGAAGAGTATGAGTATTCAACATTTCCGTGTCGCCCTTATTCCC
TTTTTTGCGGCATTTTGCCTTCCTGTTTTTGCTCACCCAGAAACGCTGGTGAAAGTAAAAGATGCTGAAGATCAGTTGGGTGCACGAGT
GGGTTACATCGAACTGGATCTCAACAGCGGTAAGATCCTTGAGAGTTTTCGCCCCGAAGAACGTTCTCCAATGATGAGCACTTTTAAAG
TTCTGCTATGTGGCGCGGTATTATCCCGTGTTGACGCCGGGCAAGAGCAACTCGGTCGCCGCATACACTATTCTCAGAATGACTTGGTT
GAGTACTCACCAGTCACAGAAAAGCATCTTACGGATGGCATGACAGTAAGAGAATTATGCAGTGCTGCCATAACCATGAGTGATAACAC
TGCGGCCAACTTACTTCTGACAACGATCGGAGGACCGAAGGAGCTAACCGCTTTTTTGCACAACATGGGGGATCATGTAACTCGCCTTG
ATCGTTGGGAACCGGAGCTGAATGAAGCCATACCAAACGACGAGCGTGACACCACGATGCCTGTAGCAATGGCAACAACTTTGCGCAAA
CTATTAACTGGCGAACTACTTACTCTAGCTTCCCGGCAACAATTAATAGACTGGATGGAGGCGGATAAAGTTGCAGGACCACTTCTGCG
CTCGGCCCTTCCGGCTGGCTGGTTTATTGCTGATAAATCTGGAGCCGTGAGCGTGGGTCTCGCGGTATCATTGCAGCACTGGGGCCAG
ATGGTAAGCCCTCCCGTATCGTAGTTATCTACACGACGGGGAGTCAGGCAACTATGGATGAACGAAATAGACAGATCGCTGAGATAGGT
GCCTCACTGATTAAGCATTGGTAACTGTCAGACCAAGTTTACTCATATATACTTTAGATTGATTTACCCCGGTTGATAATCAGAAAAGC
CCCAAAAACAGGAAGATTGTATAAGCAAATATTTAAATTGTAAACGTTAATATTTTGTTAAAATTCGCGTTAAATTTTTGTTAAATCAG
CTCATTTTTTAACCAATAGGCCGAAATCGGCAAAATCCCTTATAAATCAAAAGAATAGCCCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGGCCCACTACGTGAACCA
TCACCCAAATCAAGTTTTTTGGGGTCGAGGTGCCGTAAAGCACTAAATCGGAACCCTAAAGGGAGCCCCCGATTTAGAGCTTGACGGGG
AAAGCGAACGTGGCTACAAAGGAAGGGAAGAAAGCGAAAGGAGCGTGCCTAGGGCGCTGGCAAGTGTAGCGGTCACGCTGCGCGTAAC
CACCACACCCGCCGCGCTTAATGCGCCGCTACAGGGCGCGTAAAAGGATCTAGGTGAAGATCCTTTTTGATAATCTCATGACCAAAATC
CCTTAACGTGAGTTTTCGTTCCACTGAGCGTCAGACCCCGTAGAAAAGATCAAAGGATCTTCTTGAGATCCTTTTTTTCTGCGCGTAAT
CTGCTGCTTGCAAACAAAAAAACCACCGCTACCAGCGGTGGTTTGTTTGCCGGATCAAGAGCTACCAACTCTTTTTCCGAAGGTAACTG
GCTTCAGCAGAGCGCAGATACCAAATACTGTTCTTCTAGTGTAGCCGTAGTTAGGCCACCACTTCAAGAACTCTGTAGCACCGCCTACA
TACCTCGCTCTGCTAATCCTGTTACCAGTGGCTGCTGCCAGTGGCGATAAGTCGTGTCTTACCGGGTTGGACTCAAGACGATAGTTACC
GGATAAGGCGCAGCGGTCGGGCTGAACGGGGGGTTCGTGCACACAGCCCAGCTTGGAGCGAACGACCTACACCGAACTGAGATACCTAC
AGCGTGAGCTATGAGAAAGCGCCACGCTTCCCGAAGGGAGAAAGGCGGACAGGTATCCGGTAAGCGGCAGGGTCGGAACAGGAGAGCGC
ACGAGGGAGCTTCCAGGGGGAAACGCCTGGTATCTTTATAGTCCTGTCGGGTTTCGCCACCTCTGACTTGAGCGTCGATTTTTGTGATG
CTCGTCAGGGGGGCGGAGCCTATGGAAAAACGCCAGCAACGCGGCCTTTTTACGGTTCCTGGCCTTTTGCTGGCCTTTTGCTCACATGT
AATGTGAGTTAGCTCACTCATTAGGCACCCCAGGCTTTACACTTTATGCTTCCGGCTCGTATGTTGTGTGGAATTGTGAGCGGATAACA
ATTTCACACAGGAAACAGCTATGACCATGATTACGCCAAGCTACGTAATACGACTCACTAGGCGGCCGCGAGTCGACGAGGCCGGCCGA
TTATCGACATTGATTATTGACTAGTTATTAATAGTAATCAATTACGGGGTCATTAGTTCATAGCCCATATATGGAGTTCCGCGTTACAT
AACTTACGGTAAATGGCCCGCCTGGCTGACCGCCCAACGACCCCCGCCCATTGACGTCAATAATGACGTATGTTCCCATAGTAACGCCA
ATAGGGACTTTCCATTGACGTCAATGGGTGGAGTATTTACGGTAAACTGCCCACTTGGCAGTACATCAAGTGTATCATATGCCAAGTAC
GCCCCCTATTGACGTCAATGACGGTAAATGGCCCGCCTGGCATTATGCCCAGTACATGACCTTACGGGACTTTCCTACTTGGCAGTACA
TCTACGTATTAGTCATCGCTATTACCATGGTTCGAGGTGAGCCCCACGTTCTGCTTCACTCTCCCCATCTCCCCCCCCTCCCACCCCC
AATTTTGTATTTATTTATTTTTTAATTATTTTGTGCAGCGATGGGGGCGGGGGGGGGGGCGCGCGCCAGGCGGGGCGGGCGGGGC
GAGGGGGCGGGCGGGGCGAGGCGGAGGAGGTGCGCGGCGCAGCCAATCAGACGGACGGCGCTCCTCCCGAAAAGTTTCCTTTTATGGCGAGGCGGCG
GCGGCGGCGGCCCTATAAAAAGCGAAGCGCGCGGCGGGCGGGAGTCGCTGCGTTGCCTTCGCCCCGTGCCCCGCTCCGCGCCGCCTCGC
GCCGCCCGCCCCGGCTCTGACTGACCGCGTTACTCCCACAGGTGAGCGGGCGGGACGGCCCTTCTCCTCCGGGCTGTAATTAGCGCTTG
GTTTAATGACGGCTCGTTTCTTTTCTGTGGCTGCGTGAAAGCCTTAAAGGGCTCCGGGAGGGCCCTTTGTGCGGGGGGAGCGGCTCGG
GGGGTGCGTGCGTGTGTGTGTGCGTGGGGAGCGCGCGCGTGCGGCCGCGCTGCCGGCGGCTGTGAGCGCTGCGGGCGCGGCGCGGGGC
TTTGTGCGCTCCGCGTGTGCGCGAGGGGAGCGCGGCCTGCCCGGGCGGTGCGGGGGGCTGCGAGGGGAACAAAGGCTGCGT
GCGGGGTGTGTGCGTGGGGGGTGAGCAGGGGGTGTGGCGCGGCGGTCGGGCGTGTAACCCCCCCTGCACCCCCCTCCCGAGTTGCT
GAGCACGGCCCGGCTTCGGGTGCGGGGCTCCGTGCGGGGCGTGGCGCGGGGCTCGCCGTGCCGGGCGGGGGGTGGCGGCAGGTGGGGT
GCCGGGCGGGGCGGGGCCGCCTCGGGCCGGGGAGGGCTCGGGGGAGGGGCGCGGCGGCCCCGGAGCGCCGGCGGCTGTCGAGGCGCGGC
GAGCCGCAGCCATTGCCTTTTATGGTAATCGTGCGAGAGGGCGCAGGGACTTCCTTTGTCCCAAATCTGGCGGAGCCGAAATCTGGGAG
GCGCCGCCGCACCCCCTCTAGCGGGCGCGGGCGAAGCGGTGCGGCGCCGGCAGGAAGGAAATGGGCGGGGAGGGCCTTCGTGCGTCGCC
GCGCCGCCGTCCCCTTCTCCATCTCCAGCCTCGGGGCTGCCGCAGGGGGACGGCTGCCTTCGGGGGGACGGGGCAGGGCGGGGTTCGG
CTTCTGGCGTGTGACCGGCGGCTCTAGAGCCTCTGCTAACCATGTTCATGCCTTCTTCTTTTTCCTACAGCTCCTGGGCAACGTGCTGG
TTGTTGTGCTGTCTCATCATTTTGGCAAAGAATTCGGCCTGCAGACCATGCCAAAAAAGAAGAGAAAGGTCATGAAACCAGTAACGTTA
TACGATGTCGCAGAGTATGCCGGTGTCTCTTATCAGACCGTTTCCCGCGTGGTGAACCAGGCCAGCCACGTTTCTGCGAAAACGCGGGA
AAAAGTGGAAGCGGCGATGGCGGAGCTGAATTACATTCCCAACCGCGTGGCACAACAACTGGCGGGCAAACAGTCGTTGCTGATTGGCG
TTGCCACCTCCAGTCTGGCCCTGCACGCGCCGTCGCAAATTGTCGCGGCGATTAAATCTCGCGCCGATCAACTGGGTGCCAGCGTGGTG
GTGTCGATGGTAGAACGAAGCGGCGTCGAAGCCTGTAAAGCGGCGGTGCACAATCTTCTCGCGCAACGCGTCAGTGGGCTGATCATTAA
CTATCCGCTGGATGACCAGGATGCCATTGCTGTGGAAGCTGCCTGCACTAATGTTCCGGCGTTATTTCTTGATGTCTCTGACCAGACAC
CCATCAACAGTATTATTTTCTCCCATGAAGACGGTACGCGACTGGGCGTGGAGCATCTGGTCGCATTGGGTCACCAGCAAATCGCGCTG
TTAGCGGGCCCATTAAGTTCTGTCTCGGCGCGTCTGCGTCTGGCTGGCTGGCATAAATATCTCACTCGCAATCAAATTCAGCCGATAGC
GGAACGGGAAGGCGACTGGAGTGCCATGTCCGGTTTTCAACAAACCATGCAAATGCTGAATGAGGGCATCGTTCCCACTGCGATGCTGG
TTGCCAACGATCAGATGGCGCTGGGCGCAATGCGCGCCATTACCGAGTCCGGGCTGCGCGTTGGTGCGGATATCTCGGTAGTGGGATAC
GACGATACCGAAGACAGCTCATGTTATATATCCCGCCGTCAACCACCATCAAACAGGATTTTCGCCTGCTGGGGCAAACCAGCGTGGACCG
CTTGCTGCAACTCTCTCAGGGCCAGGCGGTGAAGGGCAATCAGCTGTTGCCCGTCTCACTGGTGAAAAGAAAAACCACCCTGGCGCCCA
ATACGCAAACCGCCTCTCCCCGCGCGTTGGCCGATTCATTAATGCAGCTGGCACGACAGGTTTCCCGACTGGAAAGCGGGCAGTGAGAA
TTCACTCCTCAGGTGCAGGCTGCCTATCAGAAGGTGGTGGCTGGTGTGGCCAATGCCCTGGCTCACAAATACCACTGAGATCTTTTCC
CTCTGCCAAAAATTATGGGGACATCATGAAGCCCCTTGAGCATCTGACTTCTGGCTAATAAAGGAAATTTATTTTCATTGCAATAGTGT
GTTGGAATTTTTTGTGTCTCTCACTCGGAAGGACATATGGGAGGGCAAATCATTTAAAACATCAGAATGAGTATTTGGTTTAGAGTTTG
GCAACATAGCCATATGCTGGCTGCCATGAACAAAGGTGCTATAAAGAGGTCATCAGTATATGAAACAGCCCCCTGCTGTCCATTCCT
TATTCCATAGAAAAGCCTTGACTTGAGGTTAGATTTTTTTATATTTTGTTTTGTGTTATTTTTTCTTTAACATCCCTAAAATTTTCC
TTACATGTTTTACTAGCCAGATTTTTCTCCTCTGACTACTCCCAGTCATAGCTGTCCCTCTTCTCTTATGAAGATCCTCGACCT
GCAGCCCAGCCCAAGCTCGGGGCCAGGTCGGCCGAGCGATCGCGAGAATTCGGCTTAAGTGAGTCGTATTACGGACTGGCCGTCGTTTT
ACAACGTCGTGACTGGGAAAACCCTGGCGTTACCCAACTTAATCGCCTTGCAGCACATCCCCCTTTCGCCAGCTGGCGTAATAGCGAAG
AGGCCCGCACCGATCGCCCTTCCCAACAGTTGCGCAGCCTGAATGGCGAATGGCGCTTCGCTTGGTAATAAAGCCCGCTTCGGCGGGCT
TTTTTTT
```

| Oligo # | Sequence (5' to 3') |
|---|---|
| 10164 | CGGAATTCACCTGCCAGACCATGCCAAAAAAGAAGAGAAAGGTCATGAAACCAGTAACGTTATACG |
| 10165 | CGGAATTCTCACTGCCCGCTTTCCAGTCG |
| 10218 | GCATTCTCGCAAGCTTCAAAAGCGCACGTCTGCCGCGCTATTGTGAGCGCTCACAATTCCGGGCCTTTCGACCTG |
| 9959 | TCATCAATTTCTGCAGAC |
| 10219 | TGCGCTTTTGAAGCTTGCGAGAATGCCGGGATTGTGAGCGCTCACAATAGGACCTTCGCGCCCGCC |
| 4201 | CAGGAAACAGCTATGAC |

FIGURE 8

```
GCGGCCGCGAGTCGACGAGGCCGGCCGATTAATTAAGGCTCgacattgattattgactag
ttattaatagtaatcaattacggggtcattagttcatagcccatatatggagttccgcgt
tacataacttacggtaaatggcccgcctggctgaccgcccaacgaccccgcccattgac
gtcaataatgacgtATgttcccatagtaacgccaatagggactttccattgacgtcaatg
ggaggagtatttacggtaaactgcccacttggcagtacatcaagtgtatcatatgccaag
tacgccccctattgacgtcaatgacggtaaatggcccgcctggcattatgcccagtacAT
GACCTTACGGGACTTTCCTACTTGGCAGTACATCTACGTATTAGTCATCGCTATTACCAT
GGTtcgaggtgagccccacgttctgcttcactctcccatctcccccctcccacccc
caattttgtatttatttatttttaattattttgtgcagcgatgggggcgggggggggggg
gggcgcgcgccaggcggggcggggcggggcgaggggcggggcggggcgaggcggagaggt
gcggcggcagccaatcagagcggcgcgctccgaaagtttcctttatggcgaggcggcgg
cggcggcggccctataaaAAGCGAAGCGCGCGGCGGGCGGGAGTCGCTGCGTTGCCTTCG
CCCCGTGCCCCGCTCCGCGCCGCCTCGCGCCGCCCGCCCCGGCTCTGACTGACCGCGTTA
CTCCCACAGGTGAGCGGGCGGGACGGCCCTTCTCCTCCGGGCTGTAATTAGCGCTTGGTT
TAATGACGGCTCGTTTCTTTTCTGTGGCTGCGTGAAAGCCTTAAAGGGCTCCGGGAGGGC
CCTTTGTGCGGGGGGGAGCGGCTCGGGGGGTGCGTGCGTGTGTGTGCGTGGGGAGCGC
CGCGTGCGGCCCGCGCTGCCCGGCGGCTGTGAGCGCTGCGGGCGCGGCGCGGGGCTTTGT
GCGCTCCGCGTGTGCGCGAGGGGAGCGCGGCCGGGGCGGTGCCCCGCGGTGCGGGGGGG
CTGCGAGGGGAACAAAGGCTGCGTGCGGGGTGTGTGCGTGGGGGGGTGAGCAGGGGTGT
GGGCGCGGCGGTCGGGCTGTAACCCCCCCCTGCACCCCCCTCCCCGAGTTGCTGAGCACG
GCCCGGCTTCGGGTGCGGGCTCCGTGCGGGCGTGGCGCGGGCTCGCCGTGCCGGGCG
GGGGGTGGCGGCAGGTGGGGGTGCCGGGCGGGCGGGGCCGCCTCGGGCCGGGGAGGGCT
CGGGGGAGGGGCGCGGCGGCCCCGGAGCGCCGGCGGCTGTCGAGGCGCGGCGAGCCGCAG
CCATTGCCTTTTATGGTAATCGTGCGAGAGGGCGCAGGGACTTCCTTTGTCCCAAATCTG
GCGGAGCCGAAATCTGGGAGGCGCCGCCGCACCCCCTCTAGCGGGCGCGGGCGAAGCGGT
GCGGCGCCGGCAGGAAGGAAATGGGCGGGGAGGGCCTTCGTGCGTCGCCGCGCCGCCGTC
CCCTTCTCCATCTCCAGCCTCGGGGCTGCCGCAGGGGACGGCTGCCTTCGGGGGGGACG
GGGCAGGGCGGGGTTCGGCTTCTGGCGTGTGACCGGCGGctctaGAGCCTCTGCTAACCA
TGTTCATGCCTTCTTCTTTTTCCTACAGctcctgggcaacgtgctggttgttgtgctgtc
tcatcatttggcaaagaattcGCCACCatggtgagcaagggcgaggagctgttcaccgg
ggtggtgcccatcctggtcgagctggacggcgacgtaaacggccacaagttcagcgtgtc
cggcgagggcgagggcgatgccacctacggcaagctgaccctgaagttcatctgcaccac
cggcaagctgcccgtgccctggcccaccctcgtgaccaccctgacctacggcgtgcagtg
cttcagccgctaccccgaccacatgaagcagcacgacttcttcaagtccgccatgcccga
aggctacgtccaggagcgcaccatcttcttcaaggacgacggcaactacaagacccgcgc
cgaggtgaagttcgagggcgacaccctggtgaaccgcatcgagctgaagggcatcgactt
caaggaggacggcaacatcctggggcacaagctggagtacaactacaacagccacaacgt
ctatatcatggccgacaagcagaagaacggcatcaaggtgaacttcaagatccgccacaa
catcgaggacggcagcgtgcagctcgccgaccactaccagcagaacacccccatcggcga
cggccccgtgctgctgcccgacaaccactacctgagcacccagtccgccctgagcaaaga
ccccaacgagaagcgcgatcacatggtcctgctggagttcgtgaccgccgcgggatcac
tctcggcatggacgagctgtacaagtaaGAATTCACTCCTCAGGTGCAGGCTGCCTATCA
GAAGGTGGTGGCTGGTGTGGCCAATGCCCTGGCTCACAAATACCACTGAGATCTTTTTCC
CTCTGCCAAAAATTATGGGGACATCATGAAGCCCCTTGAGCATCTGACTTCTGGCTAATA
AAGGAAATTTATTTTCATTGCAATAGTGTGTTGGAATTTTTTGTGTCTCTCACTCGGAAG
GACATATGGGAGGGCAAATCATTTAAAACATCAGAATGAGTATTTGGTTTAGAGTTTGGC
AACATATGCCATATGCTGGCTGCCATGAACAAAGGTGGCTATAAAGAGGTCATCAGTATA
TGAAACAGCCCCCTGCTGTCCATTCCTTATTCCATAGAAAAGCCTTGACTTGAGGTTAGA
TTTTTTTTATATTTTGTTTGTGTTATTTTTTCTTTAACATCCCTAAAATTTTCCTTAC
ATGTTTTACTAGCCAGATTTTTCCTCCTCTCCTGACTACTCCCAGTCATAGCTGTCCCTC
TTCTCTTATGAAGATCcctcgacctgcagcccaagctCGGGGCCAGGTCGGCCGAGCGAT
CGCGAGAATTCGGCTTAAGTGAGTCGTATTACGGACTGGCCGTCGTTTTACAACGTCGTG
ACTGGGAAAACCCTGGCGTTACCCAACTTAATCGCCTTGCAGCACATCCCCCTTTCGCCA
GCTGGCGTAATAGCGAAGAGGCCCGCACCGATCGCCCTTCCCAACAGTTGCGCAGCCTGA
```

FIGURE 14A

```
ATGGCGAATGGCGCTTCGCTTGGTAATAAAGCCCGCTTCGGCGGGCTTTTTTTTGGTTAA
CTACGTCAGGTGGCACTTTTCGGGGAAATGTGCGCGGAACCCCTATTTGTTTATTTTTCT
AAATACATTCAAATATGTATCCGCTCATGAGACAATAACCCTGATAAATGCTTCAATAAT
ATTGAAAAAGGAAGAGTATGAGTATTCAACATTTCCGTGTCGCCCTTATTCCCTTTTTTG
CGGCATTTTGCCTTCCTGTTTTTGCTCACCCAGAAACGCTGGTGAAAGTAAAAGATGCTG
AAGATCAGTTGGGTGCACGAGTGGGTTACATCGAACTGGATCTCAACAGCGGTAAGATCC
TTGAGAGTTTTCGCCCCGAAGAACGTTCTCCAATGATGAGCACTTTTAAAGTTCTGCTAT
GTGGCGCGGTATTATCCCGTGTTGACGCCGGGCAAGAGCAACTCGGTCGCCGCATACACT
ATTCTCAGAATGACTTGGTTGAGTACTCACCAGTCACAGAAAAGCATCTTACGGATGGCA
TGACAGTAAGAGAATTATGCAGTGCTGCCATAACCATGAGTGATAACACTGCGGCCAACT
TACTTCTGACAACGATCGGAGGACCGAAGGAGCTAACCGCTTTTTTGCACAACATGGGGG
ATCATGTAACTCGCCTTGATCGTTGGGAACCGGAGCTGAATGAAGCCATACCAAACGACG
AGCGTGACACCACGATGCCTGTAGCAATGGCAACAACGTTGCGCAAACTATTAACTGGCG
AACTACTTACTCTAGCTTCCCGGCAACAATTAATAGACTGGATGGAGGCGGATAAAGTTG
CAGGACCACTTCTGCGCTCGGCCCTTCCGGCTGGCTGGTTTATTGCTGATAAATCTGGAG
CCGGTGAGCGTGGGTCTCGCGGTATCATTGCAGCACTGGGGCCAGATGGTAAGCCCTCCC
GTATCGTAGTTATCTACACGACGGGGAGTCAGGCAACTATGGATGAACGAAATAGACAGA
TCGCTGAGATAGGTGCCTCACTGATTAAGCATTGGTAACTGTCAGACCAAGTTTACTCAT
ATATACTTTAGATTGATTTACCCCGGTTGATAATCAGAAAAGCCCCAAAAACAGGAAGAT
TGTATAAGCAAATATTTAAATTGTAAACGTTAATATTTTGTTAAAATTCGCGTTAAATTT
TTGTTAAATCAGCTCATTTTTTAACCAATAGGCCGAAATCGGCAAAATCCCTTATAAATC
AAAAGAATAGCCCGAGATAGGGTTGAGTGTTGTTCCAGTTTGGAACAAGAGTCCACTATT
AAAGAACGTGGACTCCAACGTCAAAGGGCGAAAAACCGTCTATCAGGGCGATGGCCCACT
ACGTGAACCATCACCCAAATCAAGTTTTTTGGGGTCGAGGTGCCGTAAAGCACTAAATCG
GAACCCTAAAGGGAGCCCCCGATTTAGAGCTTGACGGGGAAAGCGAACGTGGCGAGAAAG
GAAGGGAAGAAAGCGAAAGGAGCGGGCGCTAGGGCGCTGGCAAGTGTAGCGGTCACGCTG
CGCGTAACCACCACACCCGCCGCGCTTAATGCGCCGCTACAGGGCGCGTAAAAGGATCTA
GGTGAAGATCCTTTTTGATAATCTCATGACCAAAATCCCTTAACGTGAGTTTTCGTTCCA
CTGAGCGTCAGACCCCGTAGAAAAGATCAAAGGATCTTCTTGAGATCCTTTTTTTCTGCG
CGTAATCTGCTGCTTGCAAACAAAAAAACCACCGCTACCAGCGGTGGTTTGTTTGCCGGA
TCAAGAGCTACCAACTCTTTTTCCGAAGGTAACTGGCTTCAGCAGAGCGCAGATACCAAA
TACTGTTCTTCTAGTGTAGCCGTAGTTAGGCCACCACTTCAAGAACTCTGTAGCACCGCC
TACATACCTCGCTCTGCTAATCCTGTTACCAGTGGCTGCTGCCAGTGGCGATAAGTCGTG
TCTTACCGGGTTGGACTCAAGACGATAGTTACCGGATAAGGCGCAGCGGTCGGGCTGAAC
GGGGGGTTCGTGCACACAGCCCAGCTTGGAGCGAACGACCTACACCGAACTGAGATACCT
ACAGCGTGAGCTATGAGAAAGCGCCACGCTTCCCGAAGGGAGAAAGGCGGACAGGTATCC
GGTAAGCGGCAGGGTCGGAACAGGAGAGCGCACGAGGGAGCTTCCAGGGGGAAACGCCTG
GTATCTTTATAGTCCTGTCGGGTTTCGCCACCTCTGACTTGAGCGTCGATTTTTGTGATG
CTCGTCAGGGGGCGGAGCCTATGGAAAAACGCCAGCAACGCGGCCTTTTTACGGTTCCT
GGCCTTTTGCTGGCCTTTTGCTCACATGTAATGTGAGTTAGCTCACTCATTAGGCACCCC
AGGCTTTACACTTTATGCTTCCGGCTCGTATGTTGTGTGGAATTGTGAGCGGATAACAAT
TTCACACAGGAAACAGCTATGACCATGATTACGCCAAGCTACGTAATACGACTCACTAG
```

FIGURE 14B

GENE TARGETING VECTORS COMPRISING CONDITIONAL POSITIVE SELECTION MARKERS

RELATED APPLICATIONS

This application claims priority to U.S. Provisional Application No. 60/232,957, filed Sep. 15, 2000.

FIELD OF THE INVENTION

The present invention is directed to compositions and methods relating to the generation of cells and animals comprising a genetic modification or alteration of a targeted gene.

BACKGROUND OF THE INVENTION

The ability to manipulate the mammalian genome, and in particular, the ability to develop animals with specific genes altered or inactivated has been invaluable to the study of gene function. The capability to modify or inactivate a gene can lead to unexpected discoveries of a gene and/or mechanisms responsible for disease with similar manifestations in humans. These genetically engineered animals are also useful for testing drug treatments and developing gene therapy strategies. (See, e.g., Bradley A., 1993, Recent Prog. Horm. Res. 48:237–251).

Mouse mutants have provided an extremely useful source of knowledge of mammalian development, cellular biology, and physiology, and have provided models for human diseases. An example of a well-known animal having a mutated or "knock-out" gene includes mice carrying a specifically modified or disrupted form of a chloride-channel gene. These mice develop a disease closely resembling human cystic fibrosis. Other examples of mice that have proven to be particularly valuable include those with alterations of genes encoding lymphocyte-specific tyrosine kinase p56.sup.lck and Lyt-2, alpha.-Calcium Calmodulin kinase II gene, the C/EPB.alpha. gene, and the BAX gene. (See, e.g., Snowouwaert et al., 1992, Science 257:1083–1088; Dorin et al., 1992, Nature 359:211–215; U.S. Pat. No. 5,625,122; U.S. Pat. No. 5,530,178; Silva et al., 1992, Science, 257:201; Wang et al., 1995, Science, 269:1108; Knudsen et al., 1995, Science, 270:960).

Determining how a gene functions ultimately requires genetic analysis in vivo. The mouse, for example, is a proven model system for studying various aspects of in vivo genetic analysis and mammalian development. (See, e.g., Paigen K., 1995, Nature Med. 1:215–220). Understanding how mammalian genes function, including genes from humans, has relied heavily on gene targeting technologies. Gene targeting allows for the generation of mice with a specifically-altered genotype.

Genetically altering specifically-targeted DNA sequences within eukaryotic genomes relies on homologous recombination to replace normal gene sequences in a cell with modified exogenous sequences that introduce the desired mutation. Such targeted replacement of a DNA sequence occurs in only a small fraction of the treated cells, while the incoming DNA is subject most often to random integrations. (See, e.g., Bollag et al., 1989, Annu. Rev. Genet. 23:199–225). More particularly, exogenous sequences transferred into eukaryotic cells undergo homologous recombination with homologous endogenous sequences only at very low frequencies, and are so inefficiently recombined that large numbers of cells must be transfected, selected, and screened in order to generate a desired correctly targeted homologous recombinant. (See, e.g., Kucherlapati et al., 1984, Proc. Natl. Acad. Sci. (U.S.A.) 81: 3153; Smithies, O., 1985, Nature 317: 230; Song et al., 1987, Proc. Natl. Acad. Sci. (U.S.A.) 84: 6820; Doetschman et al., 1987, Nature 330: 576; Kim and Smithies, 1988, Nucleic Acids Res. 16: 8887; Shesely et al., 1991, Proc. Natl. Acad. Sci. (U.S.A.) 88: 4294; Kim et al., 1991, Gene 103: 227).

The most common approach to producing these transgenic animals involves the disruption of a target DNA sequence by insertion of a DNA construct encoding a selectable marker gene flanked by DNA sequences homologous to part of the target gene. When properly designed, the DNA construct effectively integrates into and disrupts the targeted gene via homologous recombination, thereby preventing the normal expression of an active gene product encoded by that gene.

Typically, gene targeting strategies employed to generate animals having specific mutations involve the following steps: 1) directed mutagenesis of the target gene in vitro; 2) introduction of the mutant gene into cultured embryonic stem cells; 3) screening for cell lines carrying the desired homologous recombination (i.e., gene replacement) event; and 4) generation of mice that transmit the mutant gene. (See, e.g., Capecchi, 1989, Trends In Genetics 5(3):70–76; Capecchi, 1989, Science 244(4910):1288–1292).

Directed mutagenesis of the target gene in vitro can be achieved using standard molecular biology and DNA cloning techniques. Typically, a functionally-relevant gene sequence is deleted and replaced with a selectable marker gene. The neo gene, which encodes neomycin phosphotransferase and confers cellular resistance to neomycin, G418 and related drugs, is routinely used as the selectable marker gene. In general, the deletion and replacement of the functionally-relevant gene are designed to generate a null mutation in the target gene disrupting its normal activity or function.

To introduce a mutant gene into cultured embryonic stem cells, a genetic construct or targeting vector is grown as a DNA plasmid in bacteria and then transfected into murine embryonic stem cells in vitro. The desired transfected cells, which represent a small fraction of the total cell population, are purified from those that failed to take in the vector by positively selecting for the marker gene in the transfected cells. Specifically, addition of neomycin to the culture kills untransfected cells, thus, selecting for the outgrowth of resistant transfected cells that express the neo gene. These resistant cells grow into colonies, each representing clonal populations derived from independently transfected cells.

Screening for cell lines carrying the desired homologous recombination event allows for the identification of cells in which the specific gene replacement has occurred. Given that random integration typically occurs more frequently than does homologous recombination, only a small minority of the colonies will be derived from cells having homologous gene replacement. This screening process requires that DNA samples isolated from individual cell lines be analyzed for homologous recombination, usually by the polymerase chain reaction (PCR) or DNA blot hybridization (Southern blotting).

To generate mice that transmit the mutant gene, embryonic stem cells carrying the desired homologous recombination event can be injected into mouse blastocysts. The blastocysts are then implanted into pseudopregnant females to generate chimeric mice, comprised of both mutant and wild-type cells. If the germline has been populated with mutant cells, then the targeted allele can be transmitted to subsequent generations, and the phenotypic consequences of the mutation can be assessed.

One of the most challenging aspects in generating animals comprising a targeted gene modification is the identification and isolation of the rare cell line that carries the homologous recombination event. One approach to combating this difficulty involves the addition of a negative selection step. This technique allows for the enrichment of the transfected cell population for the desired cells, relying on negative selection to specifically kill cells that carry random integrations. (See, e.g., U.S. Pat. No.: 5,627,059). In addition to the general techniques described above, this positive/negative selection (PNS) method requires the cloning of a negative selectable marker into the targeting vector and a further negative selection step. The gene encoding thymidine kinase (TK) is routinely used as the negative selection marker in the PNS method.

The PNS method involves a process in which a first drug is added to the cell population, for example, a neomycin-like drug to select for growth of transfected cells, i.e. positive selection. A second drug, such as FIAU is subsequently added to kill cells that express TK, i.e. negative selection. However, addition of the second drug can be quite toxic to the cells and may negatively affect the ability of the cells to populate the germline. (See, e.g., Yanagawa et al., 1999, *Transgenic Research* 215–221). Unfortunately, in addition to homologous recombination, many random integration events will also inactivate TK. Indeed, although the negative selection enriches the cell population for homologous recombinants, this population still predominantly contains random integration events.

Mammalian cells have a remarkable ability to support nonhomologous recombination of incoming DNA. For example, animals bearing a foreign gene randomly inserted into their genome to express a foreign protein are reported in the art. These animals are most often used to produce, for example, a pharmaceutical substance. Typically, in this process expression of the foreign gene's coding sequence is under the control of a promoter.

Previous studies demonstrated that control of eukaryotic transcriptional promoters, can be modified to respond to bacterial transcription factors. (See, e.g., Hu and Davidson, *Molecular and Cellular Biology* 10(12):6141–6151; Hu and Davidson, 1991, *Gene* 99(2):141–150; Hu and Davidson, 1987, *Cell* 48(4):555–566; Hu and Davidson, 1988, *Gene* 62(2):301–313; Hannan et al., 1993, *Gene* 130(2):233–239).

However, the method of expressing a foreign gene of interest in a mammalian cell by randomly inserting the gene into the genome of the animal is contrary to the process of gene targeting. Gene targeting relies on homologous recombination, wherein the goal is to produce an animal carrying a modified or disrupted form of a specific gene of interest.

As described above, the experimental challenge in gene targeting lies in identifying the rare colonies of cells carrying the desired mutated target gene. As it is often difficult to differentiate between random insertions and homologous recombination, a need in the art exists for methods that enhance and promote the recovery of homologous recombination events, while providing a faster, more efficient, and more reliable means for generating cells and animals having specific genes modified or disrupted.

SUMMARY OF THE INVENTION

The present invention relates to novel compositions and methods useful in the production of cells and animals having a genetic alteration or modification of a targeted DNA sequence. More particularly, the present invention provides compositions and methods that are capable of modifying a target gene in a cell with high efficiency and specificity.

The present invention provides a regulated positive selection vector (referred to herein as "targeting vector") that is capable of modifying or disrupting expression of a targeted gene. The targeting vector comprises a first sequence homologous to a portion or region of a target gene sequence and a second sequence homologous to a second portion or region of a target gene sequence. The targeting vector also includes a selectable marker cassette that comprises a selectable marker gene. Preferably, the selectable marker cassette is positioned in between the first and the second sequence homologous to a region or portion of the target gene sequence. In one aspect, the selectable marker cassette, in addition to a selectable marker gene, also comprises a sequence that initiates, directs, or mediates transcription of the selectable marker. The targeting vector also comprises a regulator that has the ability to control or regulate the expression of the selectable marker. Preferably, the regulator is positioned outside of the first or second sequence homologous to a region or portion of the target gene.

The present invention also provides novel methods of modifying a target gene. In one aspect, the present invention provides novel methods of producing cells having a disruption or modification of a target gene and generating animals comprising these genetic modifications. In accordance with this aspect, the targeting vector of the present invention is introduced into cells that are capable of homologous recombination. In this process, the transfected DNA will integrate or recombine with and replace the homologous portions of the endogenous sequence. When homologous recombination occurs between the homologous portions of the endogenous target gene, the targeting vector excluding the regulator is incorporated into the genome of the cell. However, most frequently the transfected DNA will integrate at a random site in the genome of the cell. In such a case, the targeting vector including the regulator is incorporated into a random site in the genome of the cell. The regulator inhibits or suppresses expression of the selectable marker, thus, if the regulator sequence is not incorporated into the genome of the cell by way of homologous recombination, the selectable marker is expressed. Thus, cells wherein gene targeting has occurred can be selected by way of the selection marker only. As expression of the selectable marker is under the control of the regulator, cells wherein random integration occur, do not survive the addition of the selection agent, as the regulator incorporated into a random site in the genome of the cell, blocks or inhibits expression of the selectable marker gene.

In a further aspect, the present invention provides a method of identifying cells comprising the targeted gene modification. Furthermore, methods of the present invention provide a faster and more efficient means for isolating and selecting cells comprising a targeted gene modification. More particularly, the present invention discloses methods that enhance the recovery of cells carrying homologous recombination events. A main feature of the methods of the present invention is that expression of the selectable marker is regulated or under the control of the regulator. Upon homologous recombination, the regulator is not incorporated into the genome of the cell, allowing for expression of the selectable marker and selection of the desired cells.

The present invention represents a significant improvement over the currently available methods of generating cells comprising a disruption or modification of a target gene. Furthermore, the present invention provides an increase over previous technologies in both the speed and frequency at which homologous recombination events can be recovered.

The present invention also provides cells and animals that have been modified by the methods of the present invention to contain desired mutations or genomic modifications. In a preferred embodiment, the cells of the present invention are embryonic stem cells. In another preferred embodiment of the present invention, the animals are mice.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The terms "homologous" as used herein denotes a characteristic of a DNA sequence having at least about 70 percent sequence identity as compared to a reference sequence, typically at least about 85 percent sequence identity, and preferably at least about 95 percent sequence identity as compared to a reference sequence. Most preferably, the homologous portions of the targeting vector will be 100% identical to the target DNA sequence. The percentage of sequence identity is calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least about 30 nucleotides long, and preferably at least about 50 to 100 nucleotides long.

"Disruption" or "modification" of a target gene or target sequence occurs when a fragment of a DNA sequence locates and recombines with an endogenous homologous sequence. These sequence disruptions or modifications may include insertions, missense, frameshift, deletion, or substitutions, or replacements of DNA sequence, or any combination thereof. Insertions include the insertion of entire genes which may be of animal, plant, prokaryotic, or viral or other origin. Disruption or modification, for example, can alter or replace a promoter, enhancer, or splice site of a target gene, and can alter the normal gene product by inhibiting its production partially or completely or by enhancing the normal gene product's activity.

The term, "transgenic cell", refers to a cell containing within its genome a specific gene that has been disrupted, modified, altered, or replaced completely or partially by the method of gene targeting.

As used herein, a "transgenic animal" is an animal that contains within its genome a specific gene that has been disrupted, modified, altered, or replaced completely or partially by the method of gene targeting. A transgenic animal includes both the heterozygote animal (i.e., one defective allele and one wild-type allele) and the homozygous animal (i.e., two defective alleles).

A "fragment" of a polynucleotide is a polynucleotide comprised of at least 9 contiguous nucleotides, preferably at least 15 contiguous nucleotides and more preferably at least 45 nucleotides, of coding or non-coding sequences.

A "host cell" includes an individual cell or cell culture which can be or has been a recipient for vector(s) or for incorporation of nucleic acid molecules and/or proteins. Host cells include progeny of a single host cell, and the progeny may not necessarily be completely identical (in morphology or in total DNA complement) to the original parent due to natural, accidental, or deliberate mutation. A host cell includes cells transfected with the constructs and vectors of the present invention.

The term "homologous recombination" refers to the exchange of DNA fragments between two DNA molecules or chromatids at the site of homologous nucleotide sequences, i.e., those sequences preferably having at least about 70 percent sequence identity, typically at least about 85 percent identity, and preferably at least about 90 percent identity, and most preferably 100 percent identity. Homology can be determined using a "BLASTN" algorithm, for example. It is understood that homologous sequences can accommodate insertions, deletions and substitutions in the nucleotide sequence. Thus, linear sequences of nucleotides can be essentially identical even if some of the nucleotide residues do not precisely correspond or align.

As used herein, the term "target sequence" (alternatively referred to as "target gene sequence" or "target DNA sequence" or "target gene") refers to any nucleic acid molecule or polynucleotide of any gene to be modified by homologous recombination. The target sequence includes an intact gene, an exon or intron, a regulatory sequence or any region between genes.

As used herein, the term "regulator", refers to a sequence or sequences (i.e., polynucleotide sequence or protein sequence) that regulates or controls expression of the selectable marker. The term "regulator" as used herein, excludes regulation of the expression of the selectable marker solely by degradation of RNA.

"Non-homologous integration" or "random integration", refers to the integration of DNA randomly and at any non-targeted genomic location. Non-homologous integration or random integration does not involve homologous recombination.

As used herein, the term "operably linked" includes reference to a functional linkage between a promoter and a nucleic acid sequence. The promoter sequence initiates and mediates transcription of the nucleic acid sequence.

As used herein, the term "promoter", generally refers to a regulatory region of DNA capable of initiating, directing and mediating the transcription of a nucleic acid sequence. Promoters may additionally comprise recognition sequences, such as upstream or downstream promoter or enhancer elements, which may influence the transcription rate.

BRIEF DESCRIPTION OF THE DRAWINGS

FIG. 2A and FIG. 2B schematically depict and compare the DNA arrangements involved in homologous recombination and random integration of a targeting vector.

FIG. 4A depicts a traditional positive selection method. FIG. 4B depicts the positive-negative selection method. FIG. 4C depicts the regulated positive selection method of the present invention.

FIG. 6A depicts the sequence for construct 3406 (c3406)(SEQ ID NO:13). FIG. 6B depicts an example of a target gene with domains A–E. FIG. 6C depicts the first-generation vector (Targeting Vector: PGK-neo) using a PGK-neo gene as a positive selection marker (SEQ ID NO:1). FIG. 6D depicts the second-generation targeting vector. The PGK-lacO-neo targeting vector contains the indicated base changes that introduce two lacO sites as well as a Hind III restriction enzyme site, as shown. The positions of the transcription start points (asterisks) and the methionine initiator codon ($Met_i$) is also noted. Partial sequence of the PGK promoter is shown (SEQ ID NO:2), with the bases that were deleted in the second-generation targeting vector (PGK-lacO-neo-NLS-lacI) marked with strikethrough font as shown in FIG. 6C.

FIG. 8 shows the sequences of oligonucleotides: 10164 (SEQ ID NO:4); 10165 (SEQ ID NO:5); 10218 (SEQ ID NO:6); 9959 (SEQ ID NO:7); 10219 (SEQ ID NO:8); and 4201 (SEQ ID NO:9), used to generate various constructs or vectors described in the foregoing examples.

FIG. 14A and FIG. 14B show sequences for the Pst 1 and Pac 1 sites, as described in Example 1.

DETAILED DESCRIPTION OF THE INVENTION

Figure 1:
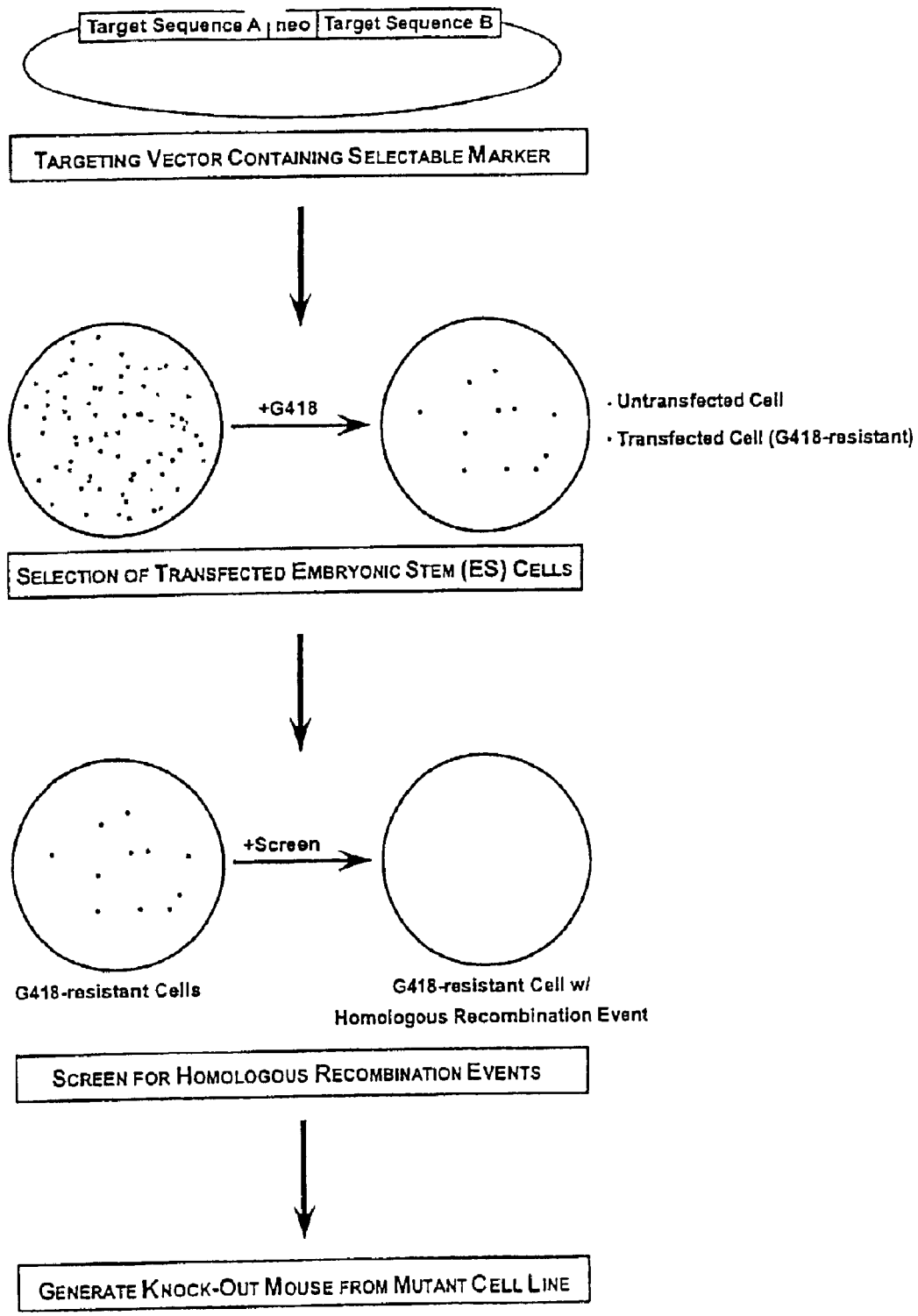
FIG. 1 illustrates a standard protocol for generating a transgenic animal. First, a targeting vector containing a selectable marker is created. Secondly, ES cells are transfected or electroporated with the targeting vector and a drug such as G418 is added to select for the transfected or electroporated cells. Next, the cells are further analyzed for homologous recombination events. The transgenic animal is generated from a cell line in which homologous recombination has occurred.

The present invention provides novel compositions and methods useful in the production of cells and animals having within the genome a specific modification of a targeted gene. More particularly, the present invention is directed to various tools and methods that provide a fast, efficient, and reliable means of generating cells and animals comprising a specific genetic modification.

Construction of the Targeting Vector

The targeting vector or construct of the present invention may be produced using standard methods known in the art. (See, e.g., Sambrook, et al., 1989, *Molecular Cloning: A Laboratory Manual*, Second Edition, Cold Spring Harbor Laboratory Press, Cold Spring Harbor, N.Y.; E. N. Glover (eds.), 1985, *DNA Cloning: A Practical Approach*, Volumes I and II; M. J. Gait (ed.), 1984, *Oligonucleotide Synthesis*; B. D. Hames & S. J. Higgins (eds.), 1985, Nucleic Acid Hybridization; B. D. Hames & S. J. Higgins (eds.), 1984, *Transcription and Translation*; R. I. Freshney (ed.), 1986, Animal Cell Culture; Immobilized Cells and Enzymes, IRL Press, 1986; B. Perbal, 1984, A Practical Guide To Molecular Cloning; F. M. Ausubel et al., 1994, *Current Protocols in Molecular Biology*, John Wiley & Sons, Inc.). For example, the targeting vector may be prepared in accordance with conventional ways, where sequences may be synthesized, isolated from natural sources, manipulated, cloned, ligated, subjected to in vitro mutagenesis, primer repair, or the like. At various stages, the joined sequences may be cloned, and analyzed by restriction analysis, sequencing, or the like.

The targeting vector or construct of the present invention typically comprises a first sequence homologous to a portion or region of a target gene sequence and a second sequence homologous to a second portion or region of the target DNA sequence. The targeting vector further comprises a selectable marker cassette comprising a sequence encoding a selectable marker, which is preferably positioned in between the first and the second DNA sequence that are homologous to a region of the target DNA sequence. The targeting vector also comprises a sequence encoding a regulator, preferably, positioned outside of the first or second DNA sequence homologous to a region or portion of the target gene.

The targeting DNA can be constructed using techniques well known in the art. For example, the targeting DNA may be produced by chemical synthesis of oligonucleotides, nick-translation of a double-stranded DNA template, polymerase chain-reaction amplification of a sequence (or ligase chain reaction amplification), purification of prokaryotic or target cloning vectors harboring a sequence of interest (e.g., a cloned cDNA or genomic DNA, synthetic DNA or from any of the aforementioned combination) such as plasmids, phagemids, YACs, cosmids, bacteriophage DNA, other viral DNA or replication intermediates, or purified restriction fragments thereof, as well as other sources of single and double-stranded polynucleotides having a desired nucleotide sequence. Moreover, the length of homology may be selected using known methods in the art. For example, selection may be based on the sequence composition and complexity of the predetermined endogenous target DNA sequence(s).

Preferably, the first and second sequences are of a functional component of a genomic sequence to be targeted. Two fragments encoding separate portions of the target gene are generated. Although the size of each flanking region is not critical and can range from as few as 100 base pairs to as many as 100 kb, preferably each flanking fragment is greater than about 1 kb in length, more preferably between about 1 and about 10 kb, and even more preferably between about 1 and about 5 kb. Although larger fragments may increase the number of homologous recombination events in ES cells, larger fragments will also be more difficult to clone.

Typically, the portion of the gene included in the targeting construct is interrupted by insertion of a marker sequence (usually a selectable marker) that disrupts the reading frame of the interrupted gene so as to preclude expression of an active gene product. This most often causes a disruption (e.g., partial or complete inactivation) of normal production, structure, or function of the polypeptide encoded by the targeted gene of a single cell, selected cells or all of the cells of an animal (or in culture).

When the targeting vectors of the present invention are introduced into embryonic stem cells, the transfected DNA can recombine with the target gene in the cell via the homologous sequences in both the vector and in the genomic region to be disrupted. The result of the homologous recombination event is often the insertion or incorporation of the selectable marker sequence into an exon or portion of an exon of the target gene. Similarly, targeting constructs designed for knocking in genes can recombine at the homologous genomic site by homologous recombination and will result in the introduction of all or a portion of a gene into that locus. Techniques for knocking in genes are described in the art. (See, e.g., Hanks et al., 1995, *Science,* 269:679.

The selectable marker is a gene encoding a product that enables only the cells that carry the gene to survive and/or grow under certain conditions. A variety of selectable markers may be used in the practice of the present invention, including, for example, genes conferring resistance to compounds such as antibiotics, and genes conferring the ability to grow on selected substrates. In one aspect, the selectable marker is an antibiotic resistance gene such as the neomycin resistance gene (neo) and the hygromycin resistance gene (hyg). (See, e.g., Southern, P., and P. Berg, 1982, *J. Mol. Appl. Genet.* 1:327–341; Te Riele, H., et al., 1990, *Nature* 348:649–651). Selectable markers that may be used in accordance with the present invention are described in the art. (See, e.g., Sambrook, J., et al., 1989, *Molecular Cloning—A Laboratory Manual*, Cold Spring Harbor Laboratory, Cold Spring Harbor, N.Y., Chapter 16). In many cases it is desirable to disrupt genes by positioning the positive selection marker in an exon, i.e., a functional component, of a gene to be disrupted or modified.

The regulator inhibits or suppresses expression of the selectable marker, and is removed upon homologous recombination, but retained upon random integration of the targeting vector. Various genetic elements are incorporated into the regulator allowing it to control expression of the selectable marker. In one aspect, the regulator comprises sequences that regulate or control the expression of the selectable marker at any step in the gene expression pathway, for example, at the point of transcription. In accordance with this aspect, the targeting vector may be comprised of a transcription control system, such as an operator/repressor system, for instance. In this construction of the targeting vector, the regulator comprises sequences that interact with or bind to sequences present within the selectable marker cassette preventing or repressing expression of the selectable marker. Other suitable transcriptional control systems capable of regulating expression of the selectable marker may be used in accordance with the present invention.

The regulator may also be comprised of elements that control expression of the selectable marker at the steps of transcription, pre-mRNA processing (i.e., splicing, polyadenylation, capping), mRNA transport, mRNA stability, translation, protein stability, and protein activity. The regulator may also comprise other sequences or DNA binding proteins that affect degradation or localization of the selectable marker or sequences, for example, a nuclear localization signal. (See, e.g., Hannan et al., *Gene* 130(2) :233–239). The regulator may also comprise sequences that direct or enhance its expression including, promoters, polyadnelyation signals, introns, and the like.

In one aspect, the selectable marker cassette comprises a selectable marker gene linked to a sequence that activates transcription of the selectable marker. In this aspect, preferably, the selectable marker cassette comprises a promoter sequence operably linked to the sequence encoding the selectable marker. The selectable marker cassette may also comprise other regulatory sequences. For example, the promoter sequence may further comprise at least one operator sequence placed adjacent to or within the promoter sequence. In this construction, the regulator interacts with or binds to the promoter/operator sequence to regulate expression of the selectable marker. In accordance with this aspect, the regulator comprises a repressor sequence compatible with the promoter/operator sequence to inhibit or repress expression of the selectable marker of the targeting vector.

A preferred design of the targeting vector includes a selectable marker cassette positioned in between the first and second sequence homologous to a portion or region of the target gene. The selectable marker cassette comprises a promoter region operably linked to a sequence encoding the selectable marker. Preferably, the selectable marker cassette further comprises at least one operator site placed adjacent to or within the promoter. In a preferred embodiment, the promoter region comprises a PGK promoter sequence and at least one operator site, and the selectable marker is the neo gene. The regulator is preferably positioned outside of and adjacent to the first or second sequence homologous to the target gene and interacts with or binds to sequences (i.e., regulatory binding sites) within the promoter region to repress or inhibit expression of the selectable marker.

Figure 6:
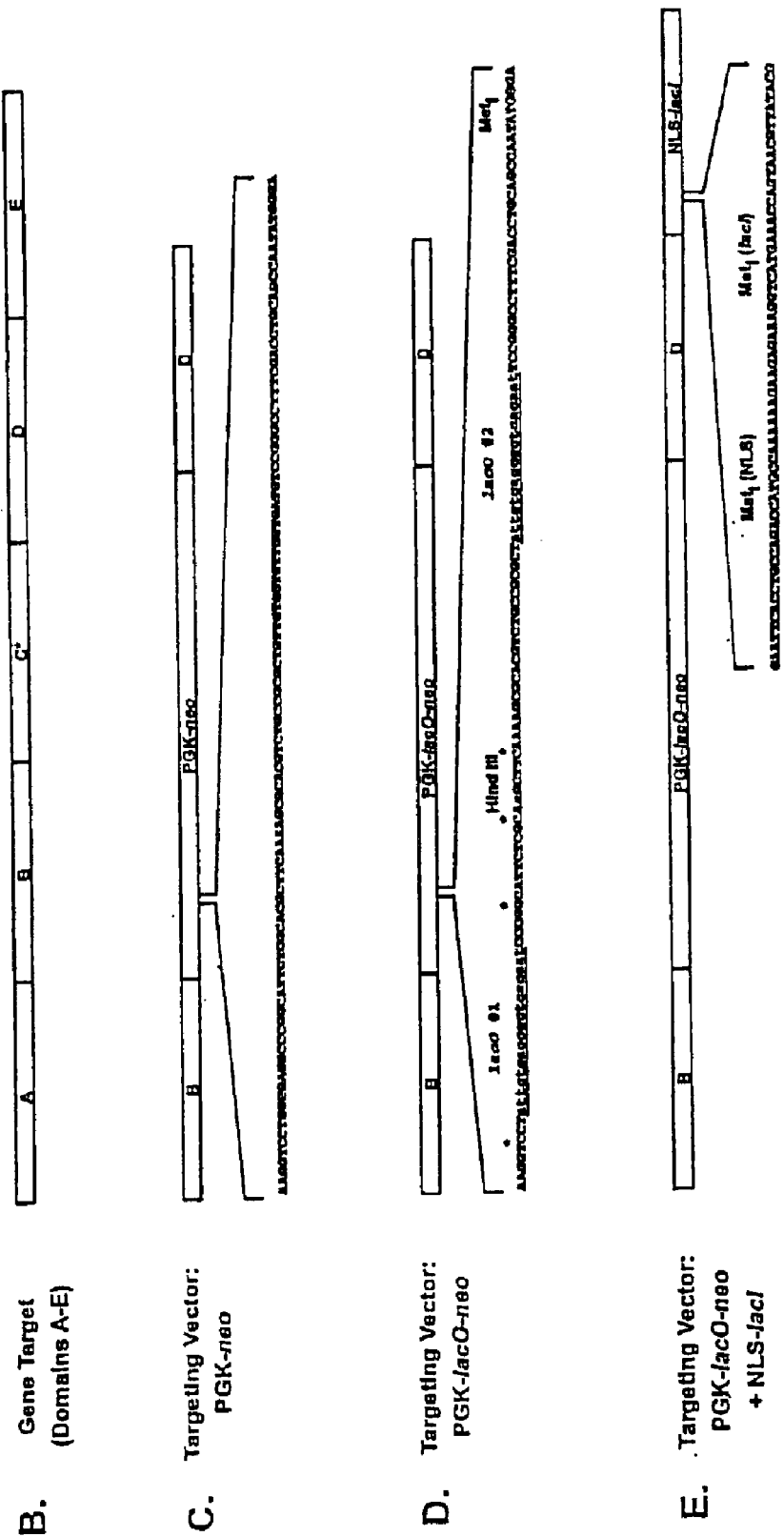
FIG. 6A through FIG. 6D schematically depict the gene targeting vectors based on the lac repressor system and display the changes in the DNA sequences that were introduced to generate these vectors.
FIG. 6E shows the final sequence of the DNA bases that encode the SV40-T antigen NLS from the methionine initiator codon of the NLS to the same codon of the lac repressor (SEQ ID NO:3).

In one aspect, the selectable marker is controlled by a lac operator/repressor system. In this design, the targeting vector comprises a selectable marker cassette comprising a promoter sequence, at least one lac operator sequence, and a sequence encoding a selectable marker, preferably, positioned in between the first and second sequences homologous to a region or portion of the target DNA. In a preferred aspect, the promoter region comprises the PGK promoter and two lac operator sequences positioned next to or within the PGK promoter sequence. The regulator is preferably positioned outside either the first or second sequences homologous to the target gene, and comprises a lac repressor sequence. In a preferred embodiment, the regulator also comprises sequences corresponding to a nuclear localization signal (NLS), resulting in a regulator that comprises sequences encoding a lac repressor and a nuclear localization signal. In a preferred embodiment, the NLS originates from the simian virus 40 large-T antigen. (See, e.g., Hu and Davidson, 1991, *Gene* 99:141–150). An example of this targeting vector is shown in FIG. 6.

Any promoter system available in the art may be used in the practice of the present invention. Examples of such promoters include the beta.-lactamase (penicillinase) system, a tryptophan (trp) promoter system, and the like. (See, e.g., Chang et al., 1978, *Nature,* 275: 615; Itakura, et al., 1977, *Science,* 198: 1056; Goeddel et al., 1979, *Nature* 281: 544; Goeddel, et al., 1980, *Nucleic Acids Res.* 8: 4057; Siebenlist, et al., 1980, *Cell* 20: 269).

Any element capable of regulating the expression of the selectable marker may be used in accordance with the present invention. Thus, the regulator may be comprised of elements other than a DNA sequence encoding a protein. The present invention contemplates that expression of the selectable marker is regulated at any step in the gene expression pathway. For example, the regulator could act in cis, for example, as a transcriptional silencer element such as NRSF/Rest, REST, MeCP2, NRF, rGH, NRE and COL4. (See, e.g., Chen et al., 1998, *Nat. Gen*; Chang et al., 1995, *Cell* 80:949–957; Xinshen-Nan et al., 1997, *Cell* 88:471–481; Nourkakhsh et al., 1997, *Immunbiolo.*; Roy et al., 1994, *Eur. J. Biochem.*; Li-Weber et al., 1993, *J. of Immunology*; Hanel et al., 1995, JBC).

Other DNA sequences or proteins that affect the uptake of the targeting vector after introduction into the cells may also be present. For example, sequences or DNA binding proteins that affect degradation or localization of the vector following entry into the targeted cells or molecules that affect the catalysis of homologous recombination may be incorporated in the targeting vector of the present invention. Moreover, other regulatory sequences may be incorporated into the targeting vector to disrupt or control expression of a particular gene in a specific cell type.

In a preferred embodiment, the targeting vector(s) of the present invention is generated in two steps. The first step involves generating a first vector comprised of a first sequence homologous to a region or portion of the target gene sequence, a second sequence homologous to a region or portion of the target gene sequence, and a third sequence that encodes a selectable marker. In the second step, standard subcloning methods known in the art may be used to incorporate the regulator into the targeting vector.

In another aspect of the present invention, a plasmid comprising: a first gene-specific region of homology; the insert containing the selectable marker, for example, a PGK-lac operator-selectable cassette; and a second gene-specific region of homology is generated. Standard subcloning methods are used to insert the regulator gene, such as a NLS-lacI sequence, into the vector. In a preferred embodiment, the selectable marker and the regulator are separated by at least one region of homology. For example, the regulator may be placed outside of and adjacent to the first or second sequence substantially homologous to the target gene.

In a preferred embodiment, the method comprises producing a targeting vector comprising a lac repressor system. As depicted in FIG. 6, a first-generation vector is produced using a PGK-neo gene as a positive selection marker. A second-generation targeting vector is produced and comprises a partial sequence of the PGK promoter containing the indicated base changes that result from introducing two laco sites, in addition to a Hind III restriction enzyme site. The positions of the transcription start points (asterisks) and the methionine initiator codon ($Met_i$) is noted in FIG. 6. A regulator comprising a sequence encoding the SV40-T antigen NLS from the methionine initiator codon of the NLS and a lac repressor is subcloned into this PGK-lacO-neo targeting vector as indicated in FIG. 6. The resulting targeting vector comprises a first and second sequence homologous to the target gene, a positive selection marker comprising a PGK-lacO-neo sequence, and a regulator comprising a NLS and lac repressor sequence.

In another embodiment of the present invention, the targeting vector is prepared directly from a plasmid genomic library using the methods described in pending U.S. patent application Ser. No.: 08/971,310, filed Nov. 17, 1997, the disclosure of which is incorporated herein in its entirety. Generally, a sequence of interest is identified and isolated from a plasmid library in a single step using, for example, long-range PCR. Following isolation of this sequence, a second polynucleotide that will disrupt the target sequence can be readily inserted between two regions encoding the sequence of interest. The regulator is subsequently subcloned into the vector.

In accordance with this embodiment, the targeting vector or construct is generated using ligation-independent cloning to insert two different fragments of the homologous sequence into a vector having a selectable marker cassette comprising the selectable marker gene positioned between the two different homologous sequence fragments in the construct. In one aspect of this embodiment, the homologous sequences may be obtained by: generating two primers complementary to the target; annealing the primers to complementary sequences in a mouse genomic DNA library containing the target region; and amplifying sequences homologous to the target region. The products of the amplification reaction, which have endpoints formed by the primers, are then isolated. Preferably, amplification is by PCR; more preferably, amplification is by long-range PCR.

Applying this method of generating the targeting vector, the present invention obviates the need for hybridization isolation, restriction mapping, and multiple cloning steps. For example, a short sequence can be used to design oligonucleotide probes that can be directly amplified to create the targeting vector. For example, a short sequence (e.g., EST) can be used to design oligonucleotide probes. These probes can be used in the direct amplification procedure to create constructs or can be used to screen genomic or cDNA libraries for longer full-length genes. Thus, it is contemplated that any gene can be quickly and efficiently prepared using the methods of the present invention for use in producing cells having a targeted gene modification.

Production and Selection of Cells Comprising a Targeted Gene Modification

Once an appropriate targeting vector(s) has been prepared, the vector may be introduced into an appropriate host cell using any method known in the art. Various techniques may be employed in the present invention, including, for example, pronuclear microinjection; retrovirus mediated gene transfer into germ lines; gene targeting in embryonic stem cells; electroporation of embryos; sperm-mediated gene transfer; and calcium phosphate/DNA co-precipitates, microinjection of DNA into the nucleus, bacterial protoplast fusion with intact cells, transfection, polycations, e.g., polybrene, polyornithine, etc., or the like (See, e.g., U.S. Pat. No. 4,873,191; Van der Putten, et al., 1985, *Proc. Natl. Acad. Sci., USA* 82:6148–6152; Thompson, et al., 1989, *Cell* 56:313–321; Lo, 1983, *Mol Cell. Biol.* 3:1803–1814; Lavitrano, et al., 1989, *Cell*, 57:717–723). Various techniques for transforming mammalian cells are known in the art. (See, e.g., Gordon, 1989, *Intl. Rev. Cytol.*, 115:171–229; Keown et al., 1989, *Methods in Enzymology*; Keown et al., 1990, *Methods and Enzymology*, Vol. 185, pp. 527–537; Mansour et al., 1988, *Nature*, 336:348–352).

In one aspect, the targeting vector is introduced into host cells by electroporation. In this process, electrical impulses of high field strength reversibly permeabilize biomembranes allowing the introduction of the vector. The pores created during electroporation permit the uptake of macromolecules such as DNA. (See, e.g., Potter, H., et al., 1984, *Proc. Nat'l. Acad. Sci. U.S.A.* 81:7161–7165).

Any cell type capable of homologous recombination may be used in the practice of the present invention. Examples of such target cells include cells derived from vertebrates including mammals such as humans, bovine species, ovine species, murine species, simian species, and ether eucaryotic organisms such as filamentous fungi, and higher multicellular organisms such as plants.

Preferred cell types are embryonic stem (ES) cells, which are typically obtained from pre-implantation embryos cultured in vitro. (See, e.g., Evans, M. J., et al., 1981, *Nature* 292:154–156; Bradley, M. O., et al., 1984, *Nature* 309:255–258; Gossler et al., 1986, *Proc. Natl. Acad. Sci. USA* 83:9065–9069; and Robertson, et al., 1986, *Nature* 322:445–448). The ES cells are cultured and prepared for introduction of the targeting vector using methods well known to the skilled artisan. (See, e.g., Robertson, E. J. ed. "Teratocarcinomas and Embryonic Stem Cells, a Practical Approach", IRL Press, Washington D.C., 1987; Bradley et al., 1986, *Current Topics in Devel. Biol.* 20:357–371; by Hogan et al. in "Manipulating the Mouse Embryo": A Laboratory Manual, Cold Spring Harbor Laboratory Press, Cold Spring Harbor N.Y., 1986; Thomas et al., 1987, *Cell* 51:503; Koller et al., 1991, *Proc. Natl. Acad. Sci. USA*, 88:10730; Dorin et al., 1992, *Transgenic Res.* 1:101; and Veis et al., 1993, *Cell* 75:229). The ES cells that will be inserted with the targeting vector are derived from an embryo or blastocyst of the same species as the developing embryo into which they are to be introduced. ES cells are typically selected for their ability to integrate into the inner cell mass and contribute to the germ line of an individual when introduced into the mammal in an embryo at the blastocyst stage of development. Thus, any ES cell line having this capability is suitable for use in the practice of the present invention.

The present invention may also be used to knockout genes in other cell types, such as stem cells. By way of example, stem cells may be myeloid, lymphoid, or neural progenitor and precursor cells. These cells comprising a disruption or knockout of a gene may be particularly useful in the study of target gene function in individual developmental pathways. Stem cells may be derived from any vertebrate species, such as mouse, rat, dog, cat, pig, rabbit, human, non-human primates and the like.

After the targeting vector has been introduced into cells, the cells where successful gene targeting has occurred are selected. Insertion of the targeting vector into the targeted gene is typically detected by selecting cells for expression of the marker gene. The cells transformed with the targeting vector of the present invention are subjected to treatment with an appropriate agent that selects against cells not expressing the selectable marker. Only those cells expressing the selectable marker gene survive and/or grow under certain conditions. For example, cells that express the introduced neomycin resistance gene are resistant to the compound G418, while cells that do not express the neo gene marker are killed by G418. The targeting vector of the present invention is constructed so that the regulator is disposed of or degraded by the cell upon homologous recombination, and thus, expression of the selectable marker is permitted. Upon random integration, substantially all of the targeting vector, including the regulator, may be incorporated into a random site in the genome of the cell and expression of the selectable marker is inhibited or repressed by the regulator.

Integration of the transfected DNA into the appropriate site of the genome results in the stable acquisition and expression of the selectable marker, wherein the first and second DNA sequences of the targeting vector are incorporated within the homologous portions of the endogenous target DNA of the cell. The targeting vector is constructed, so that upon homologous recombination, the regulator is not incorporated into the genome of the cell. Non-incorporation of the regulator allows expression of the selectable marker, and thus, identification of cells, wherein gene targeting has occurred. Predominantly, however, integration of the transfected DNA occurs at a random site in the genome of the cell. When random integration occurs, the targeting vector including the regulator is inserted into a random site in the genome of the cell. As expression of the selectable marker is under the control of the regulator, the cells wherein random integration occurs do not survive addition of the selective agent, as the regulator incorporated into the cell-blocks or inhibits expression of the marker gene.

Figure 7:
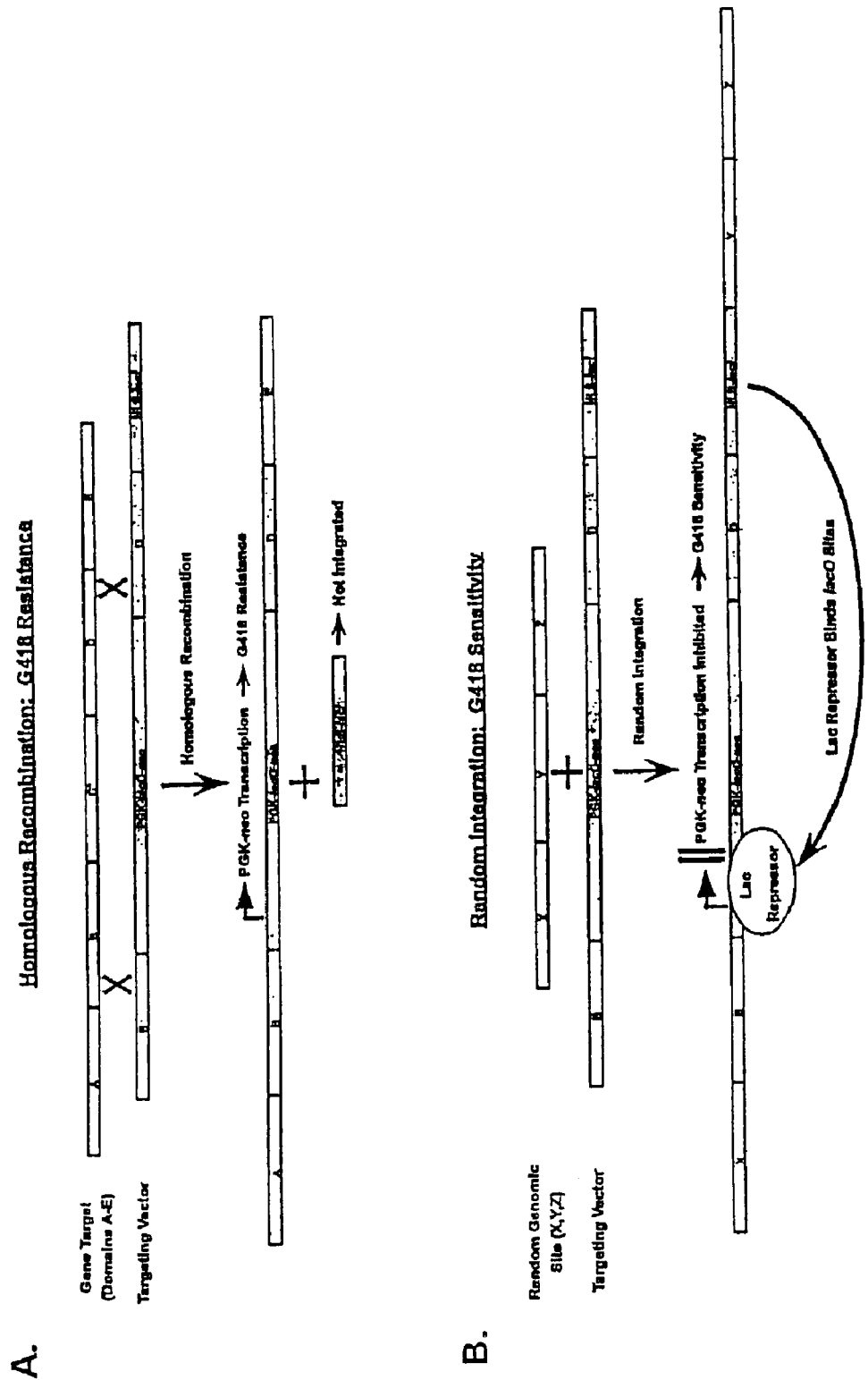
FIG. 7A and FIG. 7B illustrate the mechanism of the present invention by which cells are selected for homologous recombination using the lac repressor system.

As illustrated in FIG. 7, upon homologous recombination, lac repressor inhibition of neo transcription is relieved upon homologous recombination. The cells expressing the selectable marker can be identified through the addition of a drug, such as G418. Conversely, upon random integration, the regulator is incorporated into a random site in the genome of cells and thus, retains the ability to inhibit or suppress expression of the selectable marker. As a result of random integration of the targeting vector, the regulator interacts with the promoter operably linked to the selectable marker to inhibit transcription of the selectable marker gene. Addition of the selection agent kills these cells. More specifically, after using electroporation to place the vectors into cultured ES cells, neomycin was added to the culture medium to select for the growth of cells expressing the neo gene. Expression of the neo gene requires that: (1) the cell was successfully electroporated; and (2) lac repressor inhibition of neo transcription was relieved, i.e., by homologous recombination. This vector is then introduced into ES cells where a single positive selection selects for transfected cells and enriches the population for clones derived from the desired homologous recombination event as described below.

Successful recombination may be identified by analyzing the DNA of the selected cells to confirm homologous recombination. Various techniques known in the art, such as PCR and/or Southern analysis may be used to confirm homolgous recombination events.

The PCR screening procedure uses a target gene specific oligonucleotide that is not present on the targeting vector and an oligonucleotide corresponding to sequences in the selectable marker cassette. Oligonucleotides outside the targeting vector are used to differentiate homologous recombinants from random integrations of the targeting vector. In general, oligonucleotides not present on the targeting vector are tested on wild type ES cell DNA in combination with target gene-specific oligonucleotides that are adjacent to the insertion site of the selectable marker cassette. Oligonucleotides producing background bands or failing to give the predicted size product are eliminated. A single target gene-specific oligonucleotide is selected and paired with an oligonucleotide corresponding to sequences in the selectable marker cassette. ES cells that are PCR positive in this screen are confirmed by a second PCR experiment that utilizes a different pair of target gene-specific and selectable marker-specific oligonucleotides that are adjacent to, but distinct from, the original oligonucleotide pair. In addition, this protocol may be repeated using oligonucleotides specific for target gene sequences located on the opposite side of the selectable marker in conjunction with a marker-specific oligonucleotide. In this way proper integration (i.e., homologous recombination) of both homologous sequences of the targeting vector is verified.

Southern analysis may also be used to confirm the ES cell targeting event. A unique probe that is external to the targeting sequences themselves is developed and used to screen by Southern analysis. The probe should not contain any repetitive DNA elements and can be upstream or downstream from the targeting construct. The probe can be used in conjunction with Southern analysis of each ES clone to determine whether or not a targeting event has occurred. In addition to defining a homologous recombination DNA fragment, Southern analysis also allows for assessment of the ratio of mutant to wild-type bands, and thus an assessment of whether the ES line is a pure, clonally-derived population.

Production of Genetically Altered Animals

Embryonic stem cells which have been modified can be injected into the blastocoel of a blastocyst and grown in the uterus of a pseudopregnant female. In order to readily detect chimeric progeny, the blastocysts can be obtained from a different parental line than the embryonic stem cells. For example, the blastocysts and embryonic stem cells may be derived from parental lines with different hair color or other readily observable phenotype. The resulting chimeric animals can be bred in order to obtain non-chimeric animals which have received the modified genes through germ-line transmission. Techniques for the introduction of embryonic stem cells into blastocysts and the resulting generation of chimeric animals are well known. (See e.g., Bradley, A. "Production and analysis of chimeric mice", pp. 113–151 in Robertson, E. (ed.), *Teratocarcinomas and Embryonic Stem Cells: A Practical Approach*, Oxford IRL Press (1987); and Hogan, B., et al., 1986, Manipulating the Mouse Embryo, Cold Spring Harbor, N.Y.).

An alternate method of preparing an embryo containing ES cells that possess the targeting vector is to generate "aggregation chimeras". A morula of the proper developmental stage (about 2½ days post-fertilization for mice) is isolated. The zona pellucida can be removed by treating the morula with a solution of mild acid for about 30 seconds, thereby exposing the "clump" of cells that comprise the morula. Certain types of ES cells such as the R1 cell line for mice can then be co-cultured with the morula cells, forming an aggregation chimera embryo of morula and ES cells. (See, e.g., Joyner, A. L., 1993, *Gene Targeting, The Practical Approach Series*, JRL Press Oxford University Press, New York).

If animals homozygous for the targeted mutation are desired, they can be prepared by crossing animals heterozygous for the targeted mutation. Mammals homozygous for the disruption may be identified by Southern blotting of equivalent amounts of genomic DNA from mammals that are the product of this cross, as well as mammals of the same species that are known heterozygotes, and wild-type mammals. Alternatively, specific restriction fragment length polymorphisms can be detected which co-segregate with the mutant locus. Probes may be designed to screen the Southern blots for the presence of the targeting construct in the genomic DNA. In addition, PCRs can be used to genotype animals as wild-type, heterozygous mutant or homozygous mutant.

Other means of identifying and characterizing the offspring having a disrupted gene are also available. For example, Northern blots can be used to probe mRNA obtained from various tissues of the offspring for the presence or absence of transcripts. Differences in the length of the transcripts encoded by the targeted gene can also be detected. In addition, Western blots can be used to assess the level of expression of the targeted gene by probing the Western blot with an antibody against the protein encoded by the targeted gene. Protein for the Western blot may be isolated from tissues where this gene is normally expressed. Finally, in situ analysis (such as fixing the cells and labeling with antibody or nucleic acid probe) and/or FACS (fluorescence activated cell sorting) analysis of various cells from the offspring can be conducted using suitable antibodies to look for the presence or absence of the gene product.

Advantages

The present invention employs a regulated positive selection method that provides significant advantages over conventional methods of producing cells and animals comprising a targeted gene modification. The following compares two widely used methods of producing knockout cells and knockout animals with the regulated positive selection method of the present invention.

Figure 3:
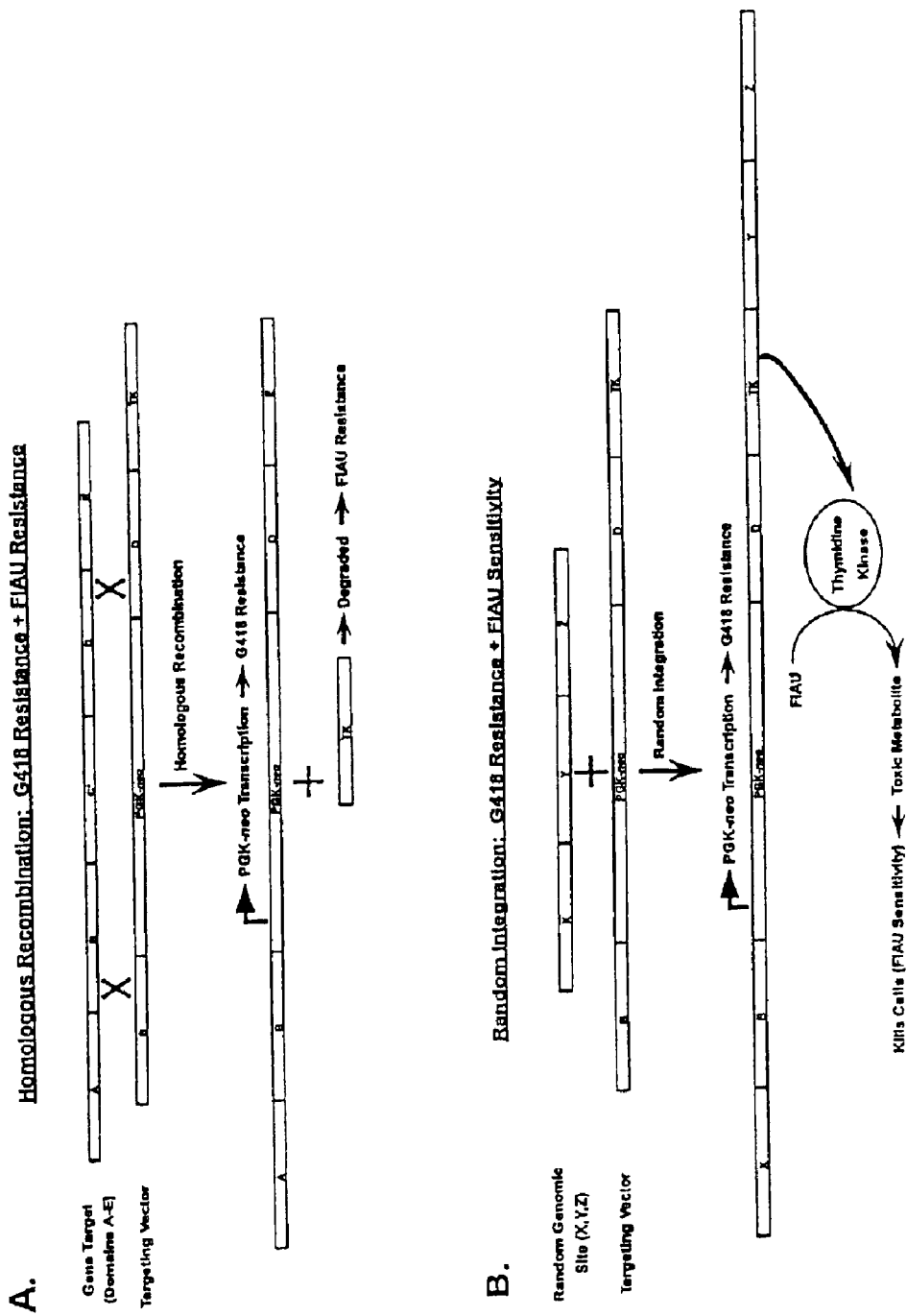
FIG. 3A and FIG. 3B illustrates the mechanism of positive-negative selection.
Figure 4:
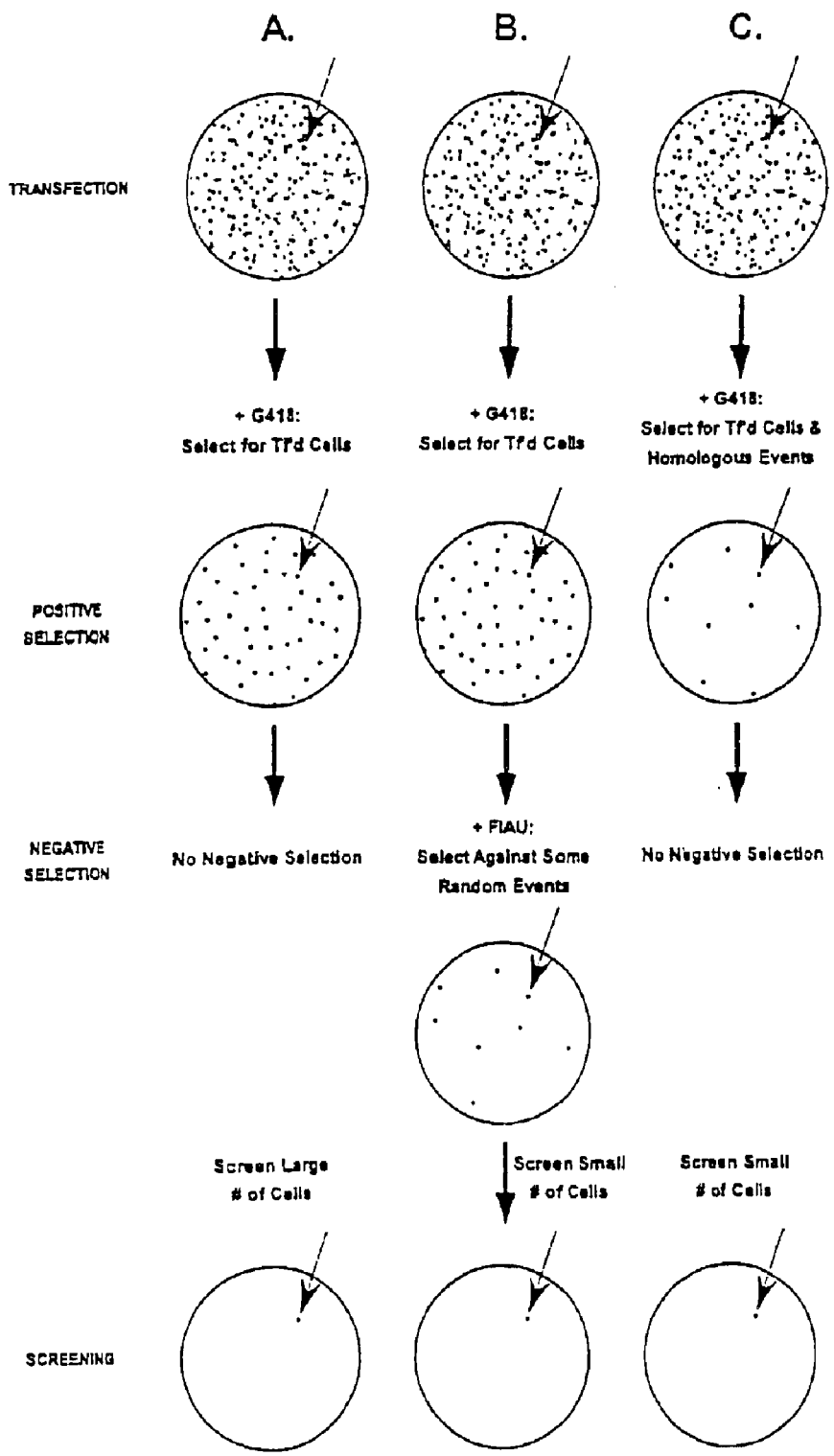
FIG. 4A through FIG. 4C depict and compare the various selection methods for identifying homologous recombination events in ES cells.
Figure 5:
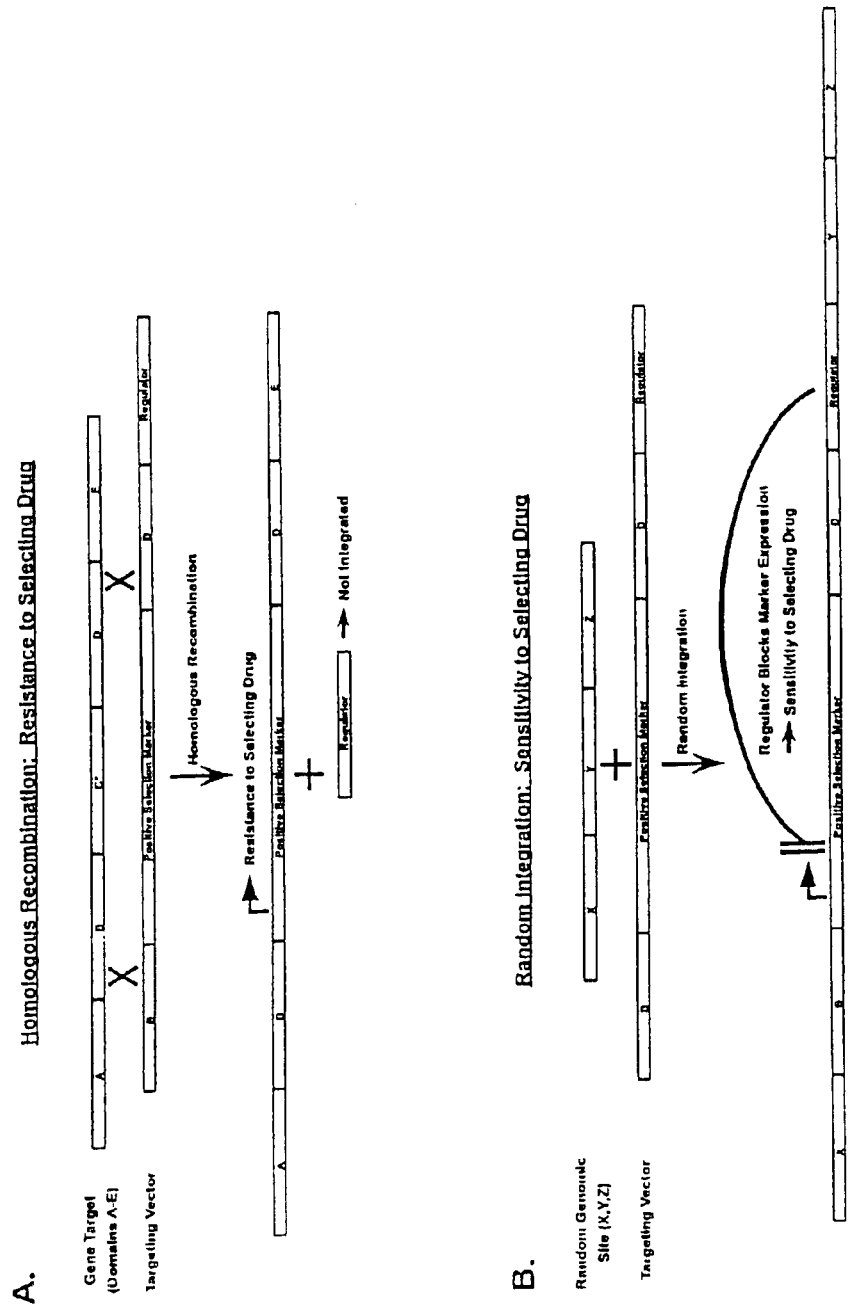
FIG. 5A and FIG. 5B depict the general mechanism of the regulated positive selection method of the present invention.

As illustrated in FIG. 3, the PNS method involves a two-step cell culturing process consisting of a positive selection step and a negative selection step. In the PNS process, a second drug, in addition to neomycin, is added that kills cells as a direct consequence of expression of the negative selection marker (See FIG. 4 and Table 1). Although this process adds to the recovery of homologous recombinants, the PNS method presents two important drawbacks. First, the two-step process may be time-consuming and laborious, and second, the addition of a second drug, such as FIAU and related drugs may hinder the ability of ES cells to populate mice and transmit the targeted allele through the germline. For example, most targeting vectors employed in the PNS method use both PGK-Neo and HSV-TK to perform positive and negative selection, respectively. However, gancyclovir treatment of ES cells is known to be quite toxic, and may negatively affect the ability of ES cells to generate animals (i.e., chimeric mice) and/or to subsequently populate the germline of these animals. Moreover, cells comprising random integration events will also inactivate expression of the negative selection marker, allowing these cells to remain present in the cell population.

Significant advantages are presented by the regulated positive method of the present invention for producing or identifying cells having a targeted gene modification as compared to the traditional positive selection method (FIG. 1) and the PNS method. The method of the present invention represents a significant improvement over both the traditional positive selection and PNS methods as the methods of the present invention enrich the cell population for homologous integration events while employing only a single drug in a one-step positive selection. Importantly, the method of the present invention allows for the selection of transfected cells and the enrichment for homologous recombinants to occur in one step with the addition of a single drug, i.e., no negative selection applied. The advantages of the methods of the present invention over the traditional positive selection method and the PNS method are summarized in the following Table I:

TABLE I

| Selection Type | Number of Steps | Number of Drugs | Screening | Side-Effects | Time/ Efforts |
| --- | --- | --- | --- | --- | --- |
| Positive | 1 | 1 | Many Colonies | None known | Slow/labor intensive: many colonies must be screened |
| PNS | 2 | 2 | Fewer Colonies | Negative selection hinders chimera generation and germline transmission; toxicity | Slow: Requires 2 drugs and is often a 2 step process |
| Regulated Positive Selection | 1 | 1 | Fewer Colonies | None known | Faster/Easier: 1 step and fewer colonies to screen |

The regulated positive selection method of the present invention clearly reveals increases over previous technologies in both the speed and frequency at which homologous recombination events can be recovered. Moreover, restricting expression of the positive selection marker to clones carrying the homologous recombination event provides a powerful means to enhance the recovery of the desired mutant cell lines without the need for additional drugs, selections, screens or cell manipulations beyond those used in the standard positive selection. Thus, the present invention provides a method that is much more rapid and efficient than currently-employed processes.

As described herein, one of the most restrictive bottlenecks in generating animals comprising a targeted gene modification is the identification and isolation of the rare cell line carrying the homologous recombination event. The present invention represents a significant improvement over the currently available methods of producing modified cells and animals having a disruption of a target gene by enriching the cell population for homologous integration events. One of the significant advantages of the present invention is that it substantially reduces the number of colonies that need be screened to identify cell lines containing a desired genetic modification. Using conventional methods, a number of random integration events would still survive and grow under positive selection. The methods of the present invention markedly reduce the number of random integration events that would normally grow under positive selection, thus, providing a more rapid and efficient process in generating cells with targeted gene modifications.

More particularly, the present invention provides methods that enhance the recovery of cell lines carrying homologous recombination events by controlling the expression of the positively-selected marker gene. Specifically, genetic elements that down regulate expression of the marker gene are cloned into the plasmid DNA adjacent to the regions that share homology with the target sequences. Homologous recombination removes these elements, which in turn increases expression of the marker gene and enhances the identification of homologous recombination events. Thus, the present invention provides fast, efficient, and reliable methods of generating cells and animals comprising a targeted gene modification.

EXAMPLES

The following examples are provided solely to illustrate the claimed invention. The present invention, however, is not limited in scope by the exemplified embodiments, which are intended as illustrations of single aspects of the invention only, and methods functionally equivalent are within the scope of the invention. Various modifications of the invention in addition to those described herein will become apparent to those skilled in the art from the foregoing description and accompanying drawings. Such modifications are intended to fall within the scope of the appended claims.

Example 1

Targeting Vector Construction

Generation of the PGK-lacO-neo Gene. The PGK-lacO-neo hybrid gene was generated in the following manner: Using pDG2 (see U.S. patent application Ser. No.: 08/971,310, filed Nov. 17, 1997) as a template, oligonucleotides 10218 and 9959 (FIG. 8) were used in the polymerase chain reaction (PCR) using Expand polymerase (Roche Biochemicals) to generate a DNA fragment containing the second lacO site (FIG. 6). This fragment was digested with Hind III and NcoI (all restriction enzymes from New England Biolabs, Beverly, Mass.). In parallel, the same reaction conditions—except using oligonucleotides 10219 and 4201—were used to generate another DNA fragment containing the first lacO site (FIG. 6). This fragment was digested with Hind III and Eco RI. The two PCR fragments were then ligated together into the Nco I and Eco RI sites of pDG2, replacing the wild-type sequence between these restriction sites. This plasmid was designated as construct 3363.

Generation of NLS-lacI Gene. The NLS-lacI gene was generated in the following manner: Using plasmid pTrcHisA (Invitrogen, Carlsbad, Calif.) as a template, oligonucleotides 10164 and 10165 (FIG. 8) were used in the polymerase chain reaction (PCR) using Expand polymerase (Roche Biochemicals) to generate a DNA fragment containing the lacI gene. The cycling conditions followed the supplier's recommendations and were as follows: 25 cycles at 94° C. for 10 seconds, 50° C. for 30 seconds and 68° C. for 70 seconds. These cycles were preceded by one denaturation heating at 94° C. for 2 minutes and were followed by an incubation at 68° C. for 7 minutes. The PCR fragment was digested with Eco RI and then subcloned into the Eco RI sites of pCX-EGFP (see Hadjantonakis et al., 1998, *Mech Dev* 76:79–90), generating construct 3359. Construct 3361 was also made, identical to c3359 except that the NLS-lacI gene is present in the reverse orientation. Finally, c3359 was digested with Sal I and Hind III, the DNA ends were made blunt using T4 DNA polymerase (Roche Biochemicals), and the DNA fragment containing NLS-lacI and the surrounding enhancer, promoter, intron and polyadenylation sequences was subcloned into the Pst I and Pac I sites (See FIGS. 14A and 14B) to generate constructs c3406 (FIG. 6A) and c3408, which are identical except that each contains the entire lac repressor expression cassette in opposite orientations.

Targeting vector comprising lac repressor system. A targeting vector based on a lac repressor system is illustrated in FIG. 6. Changes in the DNA sequences that were introduced to generate these vectors are shown. The first-generation vector (Targeting Vector: PGK-neo) uses a PGK-neo gene as a positive selection marker. Partial sequence of the PGK promoter is shown, with the bases that were deleted in the second-generation targeting vector (PGK-lacO-neo-NLS-lacI) marked with strikethrough font. The PGK-lacO-neo targeting vector contains the indicated base changes that introduce two lacO sites as well as a Hind III restriction enzyme site. The positions of the transcription start points (asterisks) and the methionine initiator codon ($Met_i$) is also noted. The final sequence lists the DNA bases that encode the SV40-T antigen NLS from the methionine initiator codon of the NLS to the same codon of the lac repressor.

Example 2

Repression of PGK-lacO-neo Expression in Mouse ES Cells

Figure 9:
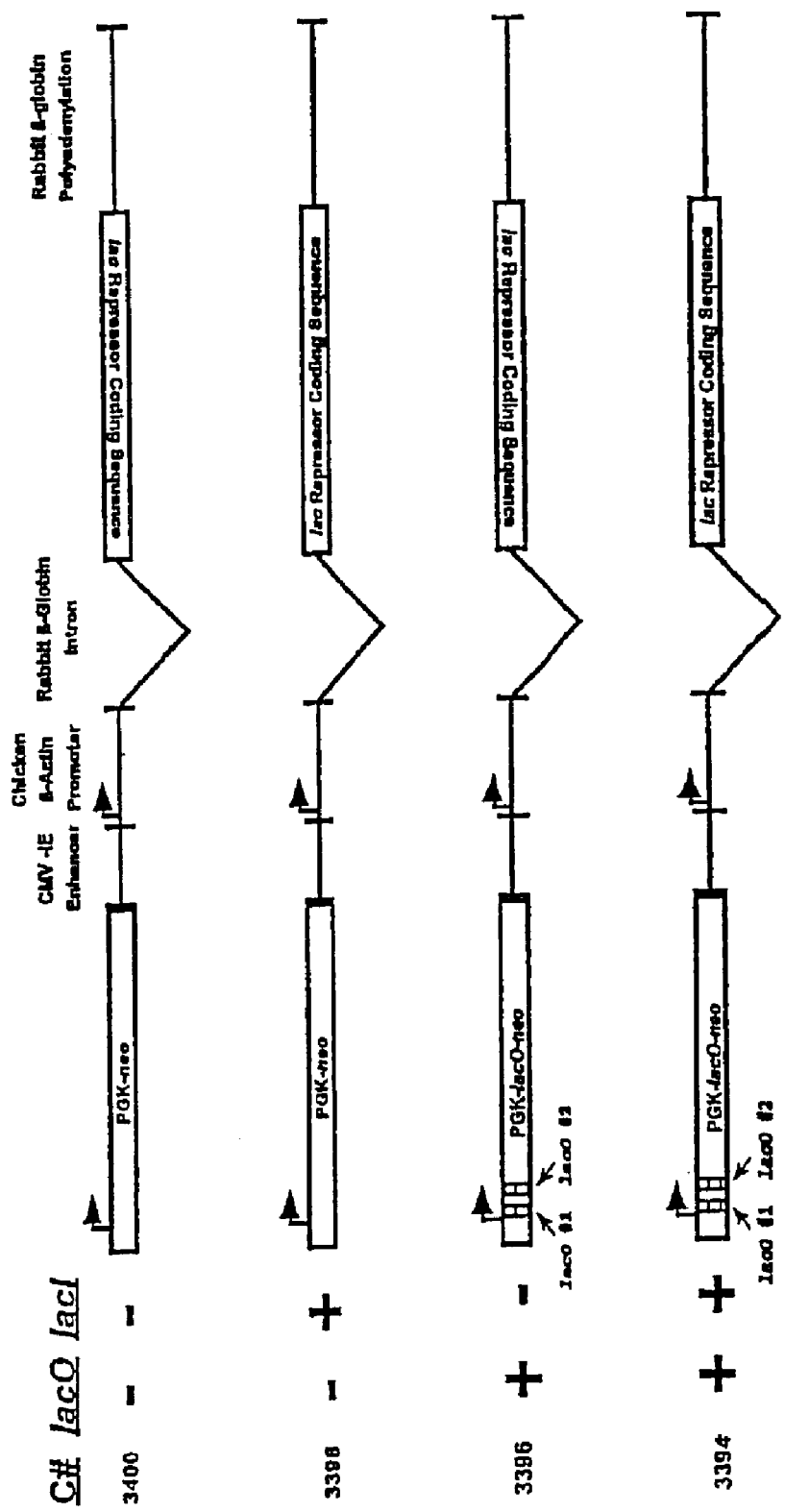
FIG. 9 schematically depicts four constructs used to test lacI repression of PGK-lacO-neo expression in mouse ES cells.

Four test vectors identified as c3400, c3398, c3396, and c3394 were created to test repression of the selectable marker. Each vector was identical to the other except for the presence or absence of the lacO or lacI sequences (FIG. 9). The lacI sequences were ligated together with the selectable marker sequences using the Bam HI and Sal I restriction sites present in each parent vector, using the plasmid backbone from the selectable marker plasmid. The wild-type PGK-neo fragment was derived from pDG-2; PGK-lacO-neo from c3363; lacI in the coding orientation from c3359; and lacI in the non-coding orientation from c3361.

To determine whether NLS-lacI could repress expression of PGK-lacO-neo and thus decrease the number of random integration events recovered, the four constructs outlined in FIG. 9 were introduced into ES cells. The effects on neo expression were assessed by counting G418-resistant colonies. Importantly, these constructs are identical, except for the presence of lacO sites and whether NLS-lacI is cloned in the coding or non-coding orientation. By limiting the changes in the plasmids to those sequences involved in lac repression, any observed effects in neo expression can be directly attributed to the specifically introduced lacO or lacI sequences as opposed to general changes in the vector backbone or other differences outside of the lac-related sequences.

The basic protocol was as follows: the constructs were digested with Swa I to generate linear DNA. As a control for experimental variability, duplicate constructs (for each of those listed in FIG. 9) were prepared and tested in parallel on separate days. The digested plasmids were resuspended in distilled water to a concentration of 1 μg/μl and introduced into mouse ES cells using electroporation. Rapidly growing ES cells were trypsinized to make single cell suspensions. The respective targeting vectors were linearized with a restriction endonuclease and 2 μg of DNA was added to 10×10$^6$ ES cells in ES medium {High Glucose DMEM (without L-Glutamine or Sodium Pyruvate) with LIF (Leukemia Inhibitory Factor-Gibco 13275-029 "ESGRO") 1,000 units/ml, and 12% Fetal Calf Serum). Cells were placed into a 2 mm gap cuvette and electroporated on a BTX electroporator at 400 μF resistance and 200 volts. Subsequently, the cells were plated using G418 concentrations of 150 μg/ml, 200 μg/ml or 400 μg/ml. After 10–12 days of selection, the total number of G418-resistant colonies were counted.

Figure 10:
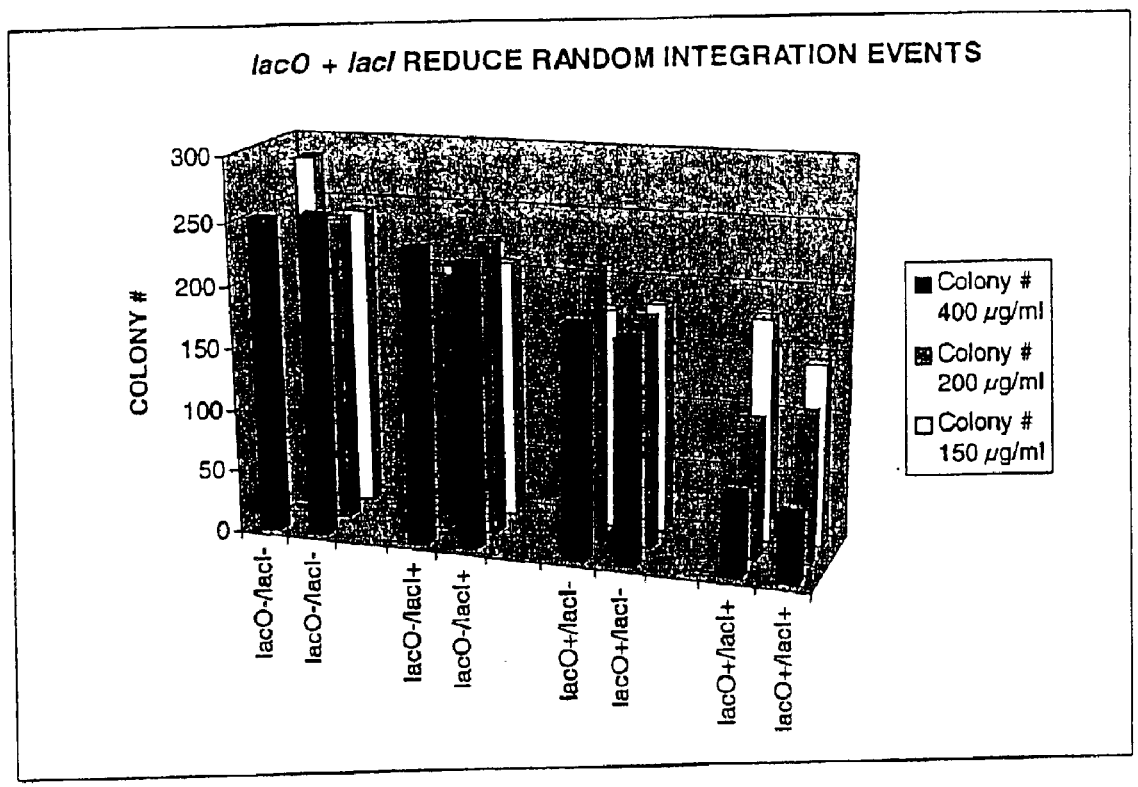
FIG. 10 shows data relating to repression of PGK-lacO-neo expression in mouse ES cells. The colony number is graphed for each of the duplicate constructs that were tested at three different concentrations of G418.

The lacI or lacO sequences alone (c3398, c3396 compared to c3400) resulted in a decrease in colony number at each concentration of G418 (FIG. 10). The lacO and lacI sequences together (c3394) also reduced the number of G418-resistant colonies. However, this reduction differed from those that resulted from lacO or lacI alone in two important ways. First, the reduction observed with c3394 was significantly larger than were the reductions observed from c3398 and c3396, particularly at the higher G418 concentrations. This result suggests that the lacO and lacI sequences act in concert to down regulate neo expression, as would be expected for a regulatory system dependent on formation of the lac operator-repressor complex. Second, the c3394-dependent reduction was enhanced at higher concentrations of G418, whereas the other reductions were not. This observation indicates that the lac repressor effectively down regulates PGK-lacO-neo expression, but does not completely block it. Thus, cells transfected with PGK-lacO-neo and expressing the lac repressor appear to express neo at a low level; at low concentrations of G418, this level of neo expression appears to be enough to support growth whereas at higher concentrations of G418 it is not. Taken together, the results for this experiment indicate that the lac repressor can inhibit PGK-lacO-neo expression in mouse ES cells, and in so doing, reduce the number of random integration events that grow under positive selection.

Example 3

Enhancement of Recovery of Homologous Recombination Events

Figure 11:
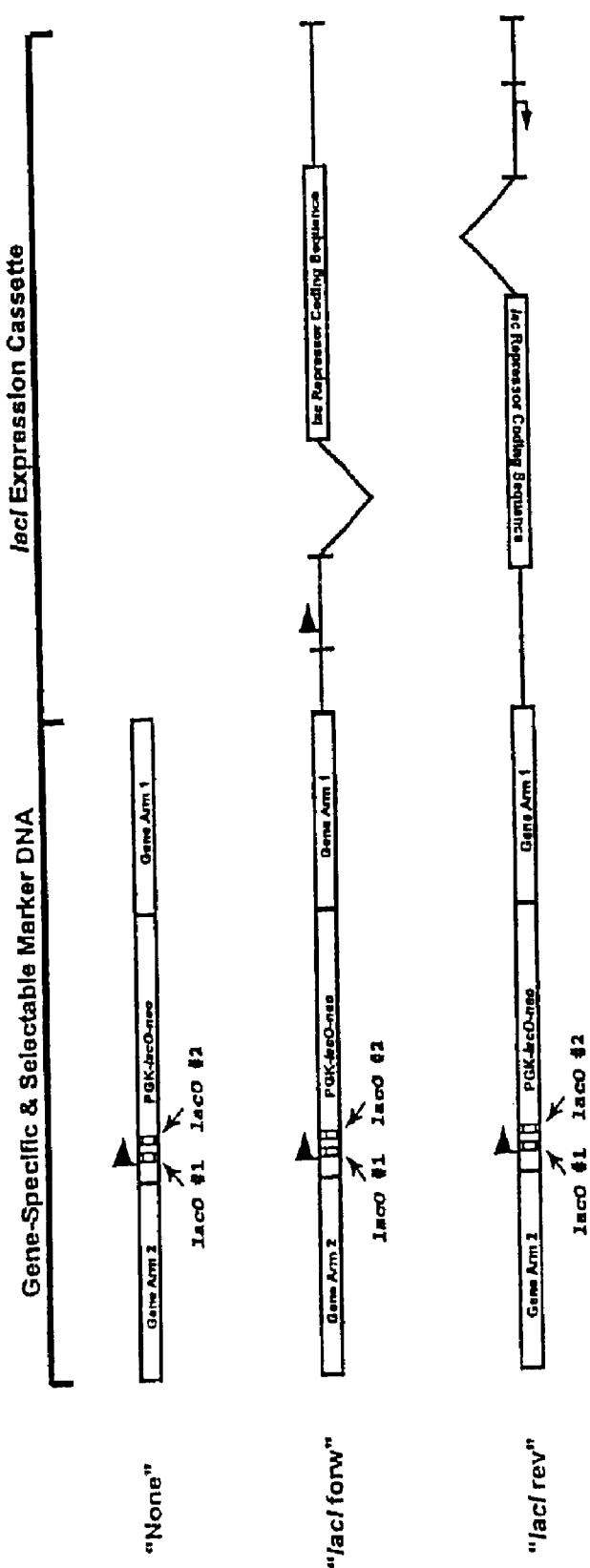
FIG. 11 schematically depicts three types of targeting vectors. The vectors all contain two gene-specific regions separated by the selectable marker, PGK-lacO-neo. "None" indicates the absence of a flanking gene; "lacI forw" and "lacI rev" indicate the presence of the lacI repressor expression cassette in the forward or reverse orientation. Both orientations express the lac repressor.

To determine whether the lac repressor system could be used to enhance the rate of recovery of homologous recombination events, three different types of targeting vectors were constructed (FIG. 11) and used to direct homologous recombination to six different target genes. These genes belonged to different gene families: serine protease, metalloprotease, serine/threonine kinase, serine protease inhibitor, G-protein-coupled receptor, and acylphosphatase.

Figure 12:
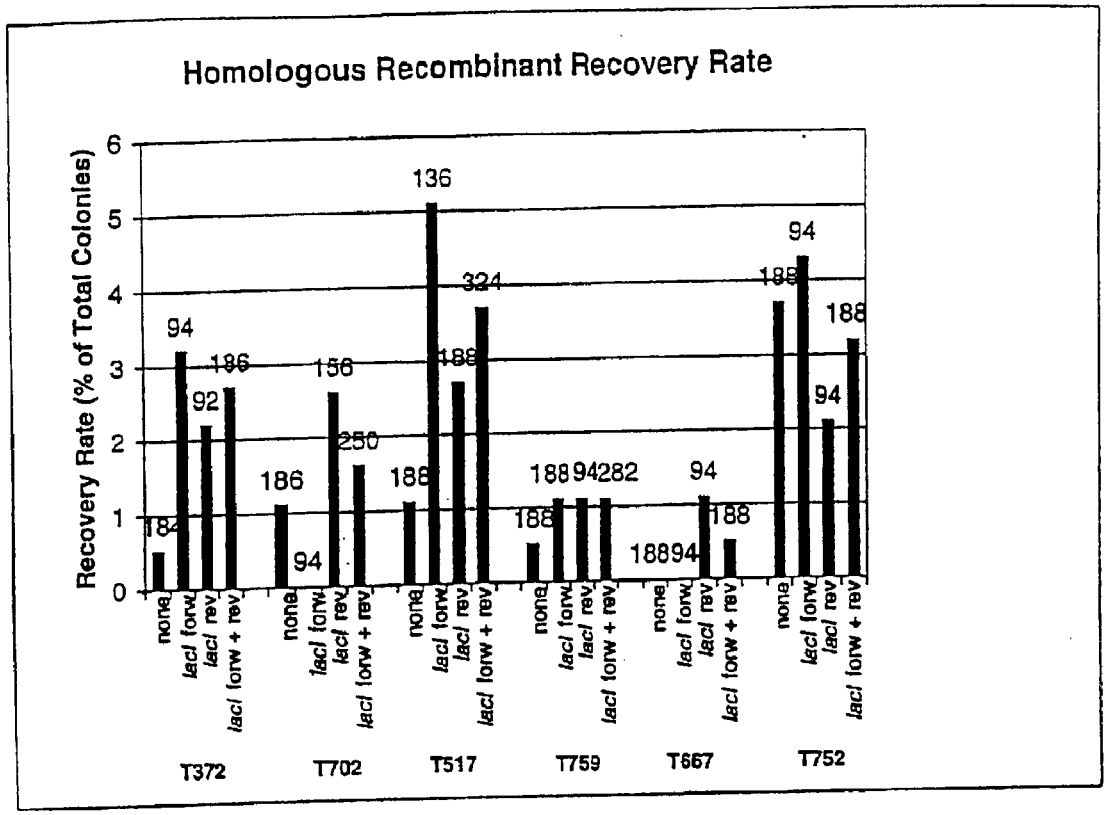
FIG. 12 shows data relating to the recovery rate of homologous recombinants graphed for each target and each targeting construct. The numbers on top of the bar graphs represent the total numbers of colonies that were screened for homologous recombination.

The results outlined in FIG. 12 clearly demonstrate that a repressor system can be used to enhance the rate at which homologous recombinants are recovered. Comparing the rates that were observed using no flanking gene ("none") to those obtained using lacI forward or reverse ("lacI forw +rev") reveals a higher rate for "lacI forw +rev" in five of the targets. The enhancement varied from approximately two- to six-fold, and in one case (T667), no homologous recombinants were detected unless the lac system was employed. In the sixth case (T752), the rates using "none" and "lacI forw +rev" were essentially equal. This target also displayed the highest recovery rate relative to the other five targets, suggesting that it may represent a recombination "hotspot" where a rate enhancement was not needed to easily detect a homologous recombination event. In summary, the results from this example reveal that the lac operator-repressor system can significantly improve upon existing methods for making targeted gene disruptions in mouse ES cells.

Example 4

Regulation of the Selectable Marker with a Silencer Element

Three copies of the NRSE silencer element derived from the S36 region of the SCG10 gene (Schoennherr and Anderson, Science, 1995) were subcloned into the Hind-III site of c319. This Hind-III site is positioned near the PGK promoter region. The sequence of the silencer element is: cagaggcactctccgtggtgctgaaa (SEQ ID NO:10)

The oligos used for cloning into the Hind-III site are the following SEQ ID NO: 11 and SEQ ID NO:12. The silencer regions for both sequences are highlighted.

AGCTTtttcagcaccacggagagtgcctctgCTtttcagcaccacggagagtgcctctgCTtttcagcaccacggagagtgcctctgA (SEQ ID NO:11)

AGCTTcagaggcactctccgtggtgctgaaaAGcagaggcactctccgtggtgctgaaaAGcagaggcactctccgtggtgctgaaaA (SEQ ID NO:12)

The number of ES cell clones which survived G418 selection between the control construct (c319) and the construct with the 3 copies of the silencer element (c 2650). Three different DNA concentrations were used under standard electroporation conditions. The concentrations were 5, 15, and 30 ug DNA.

The number of colonies after G418 selection is shown in the following Table 2:

TABLE 2

| Construct | 5 ug | 15 ug | 30 ug |
|---|---|---|---|
| PGK-Neo | 1536 | 1064 | 2180 |
| NRSE-PGK-NEO | 336 | 604 | 1848 |

Figure 13:
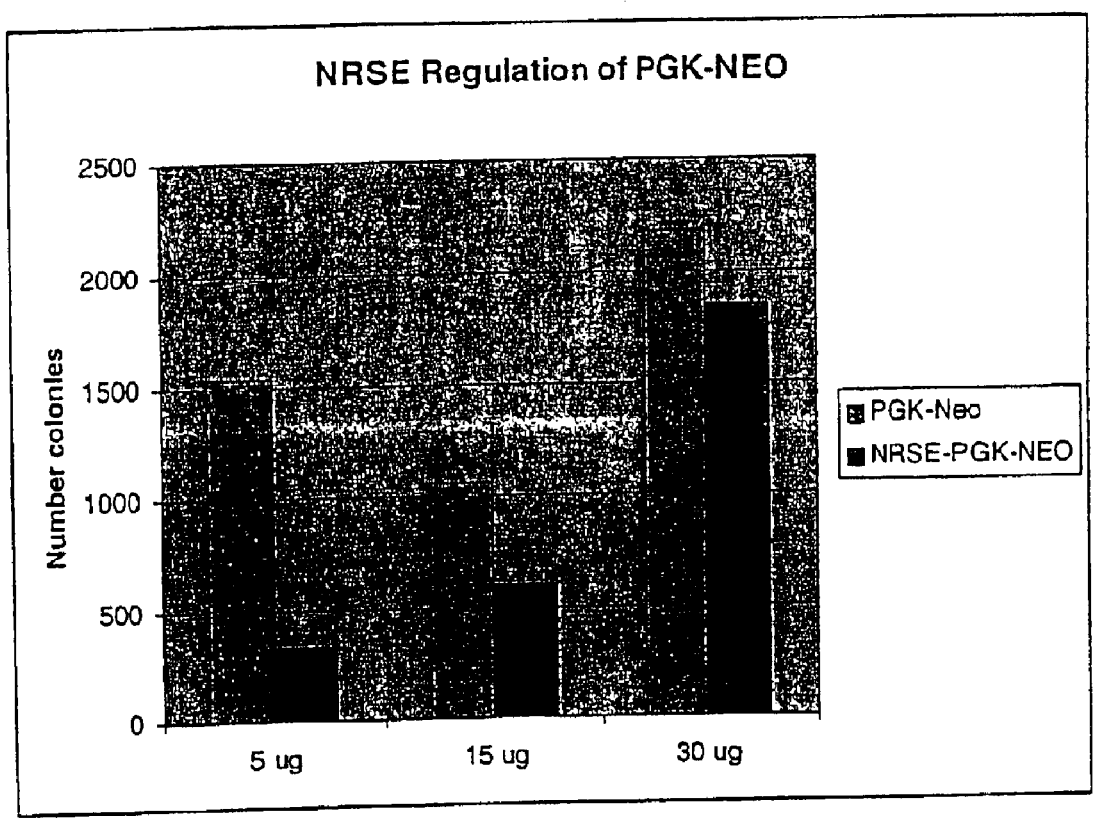
FIG. 13 shows data relating to NRSE regulation on the expression of a positive selection marker.

As shown in Table 2 and FIG. 13, there was a 78% decrease in colonies from the NRSE construct compared to the control construct at 5 ug DNA concentration; a 43% decrease in colonies from the NRSE construct compared to the control construct at 15 ug DNA concentration; and a 15% decrease in colonies from the NRSE construct compared to the control construct at 30 ug DNA concentration.

The relative increase in colony number with increasing DNA concentration may be the result of an increase in copy number or higher frequency of tandem integration events which would lead to higher levels of expression from the PGK promoter.

It is understood that the present invention is not limited to the particular methodology, protocols, cell lines, vectors, and reagents, etc., described herein, as these may vary. It is also to be understood that the terminology used herein is used for the purpose of describing particular embodiments only, and is not intended to limit the scope of the present invention. Preferred methods, devices, and materials are described, although any methods and materials similar or equivalent to those described herein can be used in the practice or testing of the present invention. All references cited herein are incorporated by reference herein in their entirety.

We claim:

1. A targeting vector capable of modifying or disrupting a target gene through homologous recombination, said vector comprising:
    a) a first sequence capable of homologously recombining with a first region of the target gene;
    b) a second sequence capable of homologously recombining with a second region of the target gene;
    c) a selectable marker cassette comprising a DNA sequence encoding a positive selection marker, said cassette located between the first sequence and second sequence; and
    d) a regulator sequence encoding an element capable of repressing expression of the DNA sequence encoding the selection marker; said regulator sequence located adjacent to the first sequence or second sequence, on a side opposite of the selectable marker cassette;
    where homologous recombination of the first sequence and second sequence with the target gene results in expression of the selection marker; and where random insertion of the vector into the target gene results in repression of the DNA sequence encoding the selection marker.

2. The targeting vector of claim 1, wherein the selectable marker cassette further comprises a promoter region.

3. The targeting vector of claim 2, wherein the selection marker is a marker conferring antibiotic resistance.

4. The targeting vector of claim 3, wherein the selection marker confers resistance to neomycin.

5. The targeting vector of claim 2, wherein the promoter region comprises a promoter sequence.

6. The targeting vector of claim 5, wherein the promoter sequence is a PGK promoter sequence.

7. The targeting vector of claim 6, wherein the promoter region further comprises at least one operator sequence.

8. The targeting vector of claim 7, wherein the operator sequence is a lac operator sequence.

9. The targeting vector of claim 6, wherein the promoter region comprises the sequence set forth in SEQ ID NO:2.

10. The targeting vector of claim 1, wherein the element encoded by the regulator sequence is a protein.

11. The targeting vector of claim 10, wherein the protein is a repressor protein.

12. The targeting vector of claim 11, wherein the repressor protein is a lac repressor protein.

13. The targeting vector of claim 12, wherein the element further comprises a nuclear localization signal.

14. The targeting vector of claim 13, wherein the regulator sequence comprises the sequence set forth in SEQ ID NO:3.

15. The targeting vector of claim 1, wherein the element encoded by the regulator sequence comprises a transcriptional silencer element.

16. The targeting vector of claim 13, wherein the sequence encoding the nuclear localization sequence is positioned upstream of the sequence encoding the repressor protein.

17. A method of producing cells comprising a modification of a target gene, the method comprising:
    a) introducing into cells capable of homologous recombination a targeting vector of claim 1;
    b) selecting for cells expressing the selection marker; and
    c) identifying cells containing the modification of the target gene.

18. The method of claim 17, wherein the cells are embryonic stem cells.

19. A method of identifying cells comprising a disruption or modification of a target gene, the method comprising:
    a) introducing into cells capable of homologous recombination a targeting vector of claim 1;
    b) selecting for cells expressing the selection marker; and
    c) identifying cells comprising the disruption or modification of the target gene.

20. The method of claim 19, wherein the cells are embryonic stem cells.

21. A method of enriching for cells comprising a disruption or modification of a target gene, the method comprising:
    a) inserting into cells capable of homologous recombination a targeting vector of claim 1;
    b) selecting for cells in which the targeting vector has integrated into the genomes of the cells via homologous recombination, wherein the selected cells express the selection marker; and
    c) identifying cells containing the disruption or modification of the target gene.

22. The method of claim 21, wherein the method enhances recovery of cells having the targeting vector integrated via homologous recombination into the genomes of the cells.

23. The method of claim 21, wherein the cells are embryonic stem cells.

24. The method of claim 21, wherein the targeting vector is introduced in the cells by electroporation.

25. A method of modifying or disrupting the function of a target DNA sequence, the method comprising introducing a targeting vector of claim 1 into a cell, thereby producing a homologous recombinant, wherein the function of the target gene is modified or disrupted.

26. The targeting vector of claim 8, wherein the element encoded by the regulator sequence is a lac repressor protein.

27. An isolated host cell comprising a modification or disruption of a target gene, wherein the target gene is modified or disrupted by insertion of the targeting vector of claim 21, into the host cell.

* * * * *

SEQUENCE LISTING

```
<160> NUMBER OF SEQ ID NOS: 14

<210> SEQ ID NO 1
<211> LENGTH: 108
<212> TYPE: DNA
<213> ORGANISM: Artificial Sequence
<220> FEATURE:
<223> OTHER INFORMATION: Targeting Vector

<400> SEQUENCE: 1
aaggtcctcc cgaggcccgg cattctcgca cgcttcaaaa gcgcacgtct gccgcgctgt      60
tctcctcttc ctcatctccg ggcctttcga cctgcagcca atatggga                  108

<210> SEQ ID NO 2
<211> LENGTH: 119
<212> TYPE: DNA
<213> ORGANISM: Artificial Sequence
<220> FEATURE:
<223> OTHER INFORMATION: Targeting Vector

<400> SEQUENCE: 2
aaggtcctat tgtgagcgct cacaatcccg gcattctcgc aagcttcaaa agcgcacgtc      60
tgccgcgcta ttgtgagcgc tcacaattcc gggcctttcg acctgcagcc aatatggga     119

<210> SEQ ID NO 3
<211> LENGTH: 64
<212> TYPE: DNA
<213> ORGANISM: Artificial Sequence
<220> FEATURE:
<223> OTHER INFORMATION: Targeting Vector

<400> SEQUENCE: 3
```

```
gaattcacct gccagaccat gccaaaaaag aagagaaagg tcatgaaacc agtaacgtta        60
tacg                                                                    64

<210> SEQ ID NO 4
<211> LENGTH: 66
<212> TYPE: DNA
<213> ORGANISM: Artificial Sequence
<220> FEATURE:
<223> OTHER INFORMATION: Primer

<400> SEQUENCE: 4
cggaattcac ctgccagacc atgccaaaaa agaagagaaa ggtcatgaaa ccagtaacgt        60
tatacg                                                                  66

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
cggaattctc actgcccgct ttccagtcg                                         29

<210> SEQ ID NO 6
<211> LENGTH: 75
<212> TYPE: DNA
<213> ORGANISM: Artificial Sequence
<220> FEATURE:
<223> OTHER INFORMATION: Primer

<400> SEQUENCE: 6
gcattctcgc aagcttcaaa agcgcacgtc tgccgcgcta ttgtgagcgc tcacaattcc        60
gggcctttcg acctg                                                        75

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
tcatcaattt ctgcagac                                                     18

<210> SEQ ID NO 8
<211> LENGTH: 66
<212> TYPE: DNA
<213> ORGANISM: Artificial Sequence
<220> FEATURE:
<223> OTHER INFORMATION: Primer

<400> SEQUENCE: 8
tgcgcttttg aagcttgcga gaatgccggg attgtgagcg ctcacaatag gaccttcgcg        60
cccgcc                                                                  66

<210> SEQ ID NO 9
<211> LENGTH: 17
<212> TYPE: DNA
<213> ORGANISM: Artificial Sequence
<220> FEATURE:
<223> OTHER INFORMATION: Primer

<400> SEQUENCE: 9
```
caggaaacag ctatgac                                                        17

<210> SEQ ID NO 10
<211> LENGTH: 26
<212> TYPE: DNA
<213> ORGANISM: Artificial Sequence
<220> FEATURE:
<223> OTHER INFORMATION: Silencer Element

<400> SEQUENCE: 10
cagaggcact ctccgtggtg ctgaaa                                              26

<210> SEQ ID NO 11
<211> LENGTH: 88
<212> TYPE: DNA
<213> ORGANISM: Artificial Sequence
<220> FEATURE:
<223> OTHER INFORMATION: Oligonucleotide Primer

<400> SEQUENCE: 11 agcttttca gcaccacgga gagtgcctct gcttttcagc accacggaga gtgcctctgc          60
ttttcagcac cacggagagt gcctctga                                            88

<210> SEQ ID NO 12
<211> LENGTH: 88
<212> TYPE: DNA
<213> ORGANISM: Artificial Sequence
<220> FEATURE:
<223> OTHER INFORMATION: Oligonucleotide Primer

<400> SEQUENCE: 12
agcttcagag gcactctccg tggtgctgaa aagcagaggc actctccgtg gtgctgaaaa          60
gcagaggcac tctccgtggt gctgaaaa                                            88

<210> SEQ ID NO 13
<211> LENGTH: 6148
<212> TYPE: DNA
<213> ORGANISM: Artificial Sequence
<220> FEATURE:
<223> OTHER INFORMATION: Construct Sequence

<400> SEQUENCE: 13
gttaactacg tcaggtggca cttttcgggg aaatgtgcgc ggaaccccta tttgtttatt          60
tttctaaata cattcaaata tgtatccgct catgagacaa taaccctgat aaatgcttca         120
ataatattga aaaggaaga gtatgagtat tcaacatttc cgtgtcgccc ttattccctt         180
ttttgcggca ttttgccttc ctgttttttgc tcacccagaa acgctggtga agtaaaaga         240 tgctgaagat cagttgggtg cacgagtggg ttacatcgaa ctggatctca acagcggtaa         300
gatccttgag agttttcgcc ccgaagaacg ttctccaatg atgagcactt ttaaagttct         360
gctatgtggc gcggtattat cccgtgttga cgccgggcaa gagcaactcg gtcgccgcat         420
acactattct cagaatgact tggttgagta ctcaccagtc acagaaaagc atcttacgga         480
tggcatgaca gtaagagaat tatgcagtgc tgccataacc atgagtgata acactgcggc         540
caacttactt ctgacaacga tcggaggacc gaaggagcta accgcttttt tgcacaacat         600
gggggatcat gtaactcgcc ttgatcgttg ggaaccggag ctgaatgaag ccataccaaa         660
cgacgagcgt gacaccacga tgcctgtagc aatggcaaca acgttgcgca aactattaac         720
tggcgaacta cttactctag cttcccggca acaattaata gactggatgg aggcggataa         780

-continued

```
agttgcagga ccacttctgc gctcggccct tccggctggc tggtttattg ctgataaatc      840
tggagccggt gagcgtgggt ctcgcggtat cattgcagca ctggggccag atggtaagcc      900
ctcccgtatc gtagttatct acacgacggg gagtcaggca actatggatg aacgaaatag      960
acagatcgct gagataggtg cctcactgat taagcattgg taactgtcag accaagttta     1020
ctcatatata ctttagattg atttaccccg gttgataatc agaaaagccc caaaaacagg     1080
aagattgtat aagcaaatat ttaaattgta acgttaata ttttgttaaa attcgcgtta      1140
aattttgtt aaatcagctc attttttaac cataggccg aaatcggcaa atcccttat        1200
aaatcaaaag aatagcccga gatagggttg agtgttgttc cagtttggaa caagagtcca     1260
ctattaaaga acgtggactc caacgtcaaa gggcgaaaaa ccgtctatca gggcgatggc     1320
ccactacgtg aaccatcacc caaatcaagt tttttgggt cgaggtgccg taaagcacta      1380
aatcggaacc ctaaagggag cccccgattt agagcttgac ggggaaagcg aacgtggcga     1440
gaaggaagg gaagaaagcg aaaggagcgg gcgctaggc gctggcaagt gtagcggtca       1500
cgctgcgcgt aaccaccaca cccgccgcgc ttaatgcgcc gctacagggc gcgtaaaagg     1560
atctaggtga agatccttt tgataatctc atgaccaaaa tcccttaacg tgagttttcg      1620
ttccactgag cgtcagaccc cgtagaaaag atcaaaggat cttcttgaga tcctttttt     1680
ctgcgcgtaa tctgctgctt gcaaacaaaa aaaccaccgc taccagcggt ggtttgtttg     1740
ccggatcaag agctaccaac tctttttccg aaggtaactg gcttcagcag agcgcagata     1800
ccaaatactg ttcttctagt gtagccgtag ttaggccacc acttcaagaa ctctgtagca     1860
ccgcctacat acctcgctct gctaatcctg ttaccagtgg ctgctgccag tggcgataag     1920
tcgtgtctta ccgggttgga ctcaagacga tagttaccgg ataaggcgca gcggtcgggc     1980
tgaacggggg gttcgtgcac acagcccagc ttggagcgaa cgacctacac cgaactgaga     2040
tacctacagc gtgagctatg agaaagcgcc acgcttcccg aagggagaaa ggcggacagg     2100
tatccggtaa gcggcagggt cggaacagga gagcgcacga gggagcttcc agggggaaac     2160
gcctggtatc tttatagtcc tgtcgggttt cgccacctct gacttgagcg tcgatttttg     2220
tgatgctcgt caggggggcg gagcctatgg aaaaacgcca gcaacgcggc cttttacgg      2280
ttcctggcct tttgctggcc ttttgctcac atgtaatgtg agttagctca ctcattaggc     2340
accccaggct ttacactta tgcttccggc tcgtatgttg tgtggaattg tgagcggata      2400
acaatttcac acaggaaaca gctatgacca tgattacgcc aagctacgta atacgactca     2460
ctaggcggcc gcgagtcgac gaggccggcc gattatcgac attgattatt gactagttat     2520
taatagtaat caattacggg gtcattagtt catagcccat atatggagtt ccgcgttaca     2580
taacttacgg taaatggccc gcctggctga ccgcccaacg accccgccc attgacgtca       2640
ataatgacgt atgttcccat agtaacgcca taggaactt ccattgacg tcaatgggag        2700
gagtatttac ggtaaactgc ccacttggca gtacatcaag tgtatcatat gccaagtacg     2760
cccctattg acgtcaatga cggtaaatgg cccgcctggc attatgccca gtacatgacc      2820
ttacgggact ttcctacttg gcagtacatc tacgtattag tcatcgctat taccatggtt     2880
cgaggtgagc cccacgttct gcttcactct ccccatctcc ccccctccc caccccaat       2940
tttgtattta tttatttttt aattattttg tgcagcgatg ggggcggggg ggggggggc      3000
gcgcgccagg cggggcgggg cgggcgagg gcgggcgg ggcgaggcgg agaggtgcgg        3060
cggcagccaa tcagagcggc gcgctccgaa agtttccttt tatggcgagg cggcggcgg      3120
ggcggcccta taaaaagcga agcgcgcggc gggcgggagt cgctgcgttg ccttcgcccc    3180
```

-continued

```
gtgccccgct ccgcgccgcc tcgcgccgcc cgccccggct ctgactgacc gcgttactcc    3240
cacaggtgag cgggcgggac ggcccttctc ctccgggctg taattagcgc ttggtttaat    3300
gacggctcgt ttcttttctg tggctgcgtg aaagccttaa agggctccgg gagggccctt    3360
tgtgcggggg ggagcggctc gggggtgcg tgcgtgtgtg tgtgcgtggg gagcgccgcg     3420
tgcggcccgc gctgcccggc ggctgtgagc gctgcgggcg cggcgcgggg ctttgtgcgc    3480
tccgcgtgtg cgcgagggga gcgcggccgg gggcggtgcc ccgcggtgcg gggggctgc    3540 gaggggaaca aaggctgcgt gcgggtgtg tgcgtggggg ggtgagcagg gggtgtgggc     3600
gcggcggtcg ggctgtaacc ccccctgca ccccctccc cgagttgctg agcacggccc     3660
ggcttcgggt gcgggctcc gtgcggggcg tggcgcgggg ctcgccgtgc cgggcggggg     3720
gtggcggcag gtgggggtgc cgggcgggc ggggccgcct cgggccgggg agggctcggg    3780
ggaggggcgc ggcggcccg gagcgccggc ggctgtcgag gcgcggcgag ccgcagccat    3840
tgccttttat ggtaatcgtg cgagagggcg cagggacttc ctttgtccca aatctggcgg    3900
agccgaaatc tgggaggcgc cgccgcaccc cctctagcgg gcgcgggcga agcggtgcgg    3960
cgccggcagg aaggaaatgg gcggggaggg ccttcgtgcg tcgccgcgcc gccgtcccct    4020
tctccatctc cagcctcggg gctgccgcag ggggacggct gccttcgggg gggacggggc    4080 agggcgggt tcggcttctg gcgtgtgacc ggcggctcta gagcctctgc taaccatgtt    4140
catgccttct tctttttcct acagctcctg gcaacgtgc tggttgttgt gctgtctcat     4200
cattttggca aagaattcac ctgccagacc atgccaaaaa agaagagaaa ggtcatgaaa    4260
ccagtaacgt tatacgatgt cgcagagtat gccggtgtct cttatcagac cgtttcccgc    4320
gtggtgaacc aggccagcca cgtttctgcg aaaacgcggg aaaaagtgga agcggcgatg    4380
gcggagctga attacattcc caaccgcgtg gcacaacaac tggcgggcaa acagtcgttg    4440
ctgattggcg ttgccacctc cagtctggcc ctgcacgcgc cgtcgcaaat tgtcgcggcg    4500
attaaatctc gcgccgatca actgggtgcc agcgtggtgg tgtcgatggt agaacgaagc    4560
ggcgtcgaag cctgtaaagc ggcggtgcac aatcttctcg cgcaacgcgt cagtgggctg    4620
atcattaact atccgctgga tgaccaggat gccattgctg tggaagctgc ctgcactaat    4680
gttccggcgt tatttcttga tgtctctgac cagacaccca tcaacagtat tattttctcc    4740
catgaagacg gtacgcgact gggcgtggag catctggtcg cattgggtca ccagcaaatc    4800
gcgctgttag cgggcccatt aagttctgtc tcggcgcgtc tgcgtctggc tggctggcat    4860
aaatatctca ctcgcaatca aattcagccg atagcggaac gggaaggcga ctggagtgcc    4920
atgtccggtt ttcaacaaac catgcaaatg ctgaatgagg gcatcgttcc cactgcgatg    4980
ctggttgcca acgatcagat ggcgctgggc gcaatgcgcg ccattaccga gtccgggctg    5040
cgcgttggtg cggatatctc ggtagtggga tacgacgata ccgaagacag ctcatgttat    5100
atcccgccgt caaccaccat caaacaggat tttcgcctgc tggggcaaac cagcgtggac    5160
cgcttgctgc aactctctca gggccaggcg gtgaagggca atcagctgtt gcccgtctca    5220
ctggtgaaaa gaaaaaccac cctggcgccc aatacgcaaa ccgcctctcc ccgcgcgttg    5280
gccgattcat taatgcagct ggcacgacag gtttcccgac tggaaagcgg gcagtgagaa    5340
ttcactcctc aggtgcaggc tgcctatcag aaggtggtgg ctggtgtggc caatgccctg    5400
gctcacaaat accactgaga tcttttttccc tctgccaaaa attatgggga catcatgaag    5460
ccccttgagc atctgacttc tggctaataa aggaaattta ttttcattgc aatagtgtgt    5520
```

```
tggaatttttt tgtgtctctc actcggaagg acatatggga gggcaaatca tttaaaacat    5580
cagaatgagt atttggttta gagtttggca acatatgcca tatgctggct gccatgaaca    5640
aaggtggcta taaagaggtc atcagtatat gaaacagccc cctgctgtcc attccttatt    5700
ccatagaaaa gccttgactt gaggttagat ttttttttata ttttgttttg tgttattttt    5760
ttctttaaca tccctaaaat tttccttaca tgttttacta gccagatttt tcctcctctc    5820
ctgactactc ccagtcatag ctgtccctct tctcttatga agatccctcg acctgcagcc    5880
cagcccaagc tcggggccag gtcggccgag cgatcgcgag aattcggctt aagtgagtcg    5940
tattacggac tggccgtcgt tttacaacgt cgtgactggg aaaaccctgg cgttacccaa    6000
cttaatcgcc ttgcagcaca tccccctttc gccagctggc gtaatagcga agaggcccgc    6060
accgatcgcc cttcccaaca gttgcgcagc ctgaatggcg aatggcgctt cgcttggtaa    6120
taaagcccgc ttcggcgggc ttttttttt                                       6148
```

<210> SEQ ID NO 14
<211> LENGTH: 5759
<212> TYPE: DNA
<213> ORGANISM: Artificial Sequence
<220> FEATURE:
<223> OTHER INFORMATION: Construct Sequence

<400> SEQUENCE: 14

```
gcggccgcga gtcgacgagg ccggccgatt aattaaggct cgacattgat tattgactag     60
ttattaatag taatcaatta cggggtcatt agttcatagc ccatatatgg agttccgcgt    120
tacataactt acggtaaatg gcccgcctgg ctgaccgccc aacgaccccc gcccattgac    180
gtcaataatg acgtatgttc ccatagtaac gccaataggg actttccatt gacgtcaatg    240
ggaggagtat ttacggtaaa ctgcccactt ggcagtacat caagtgtatc atatgccaag    300 tacgcccccct attgacgtca atgacggtaa atggcccgcc tggcattatg cccagtacat    360
gaccttacgg gactttccta cttggcagta catctacgta ttagtcatcg ctattaccat    420
ggttcgaggt gagccccacg ttctgcttca ctctccccat ctcccccccc tccccacccc    480 caatttgta tttatttatt ttttaattat tttgtgcagc gatggggggcg gggggggggg    540 gggcgcgcgc caggcggggc ggggcggggc gaggggcggg gcggggcgag gcggagaggt    600
gcggcggcag ccaatcagag cggcgcgctc cgaaagtttc cttttatggc gaggcggcgg    660
cggcggcggc cctataaaaa gcgaagcgcg cggcgggcgg gagtcgctgc gttgccttcg    720
ccccgtgccc cgctccgcgc cgcctcgcgc cgcccgcccc ggctctgact gaccgcgtta    780
ctcccacagg tgagcgggcg ggacggcccc tctcctccgg gctgtaatta gcgcttggtt    840
taatgacggc tcgtttcttt tctgtggctg cgtgaaagcc ttaaagggct ccgggagggc    900
cctttgtgcg ggggggagcg gctcgggggg tgcgtgcgtg tgtgtgtgcg tggggagcgc    960
cgcgtgcggc ccgcgctgcc cggcggctgt gagcgctgcg ggcgcggcgc ggggctttgt   1020
gcgctccgcg tgtgcgcgag gggagcgcgg ccggggggcgg tgccccgcgg tgcggggggg   1080
ctgcgagggg aacaaaggct gcgtgcgggg tgtgtgcgtg gggggggtgag caggggggtgt   1140 gggcgcggcg gtcgggctgt aacccccccc tgcaccccc ccccgagtt gctgagcacg    1200 gcccggcttc gggtgcgggg ctccgtgcgg ggcgtgcgc ggggctcgcc gtgccgggcg   1260 ggggtggcg gcaggtgggg gtgccggggcg gggcggggcc gcctcgggcc ggggagggct   1320 cggggggaggg gcgcggcggc cccggagcgc cggcggctgt cgaggcgcgg cgagccgcag   1380
ccattgcctt ttatggtaat cgtgcgagag ggcgcaggga cttcctttgt cccaaatctg   1440
```

```
gcggagccga aatctgggag gcgccgccgc accccctcta gcgggcgcgg gcgaagcggt    1500
gcggcgccgg caggaaggaa atgggcgggg agggccttcg tgcgtcgccg cgccgccgtc    1560
cccttctcca tctccagcct cggggctgcc gcagggggac ggctgccttc ggggggggacg   1620 gggcagggcg gggttcggct tctggcgtgt gaccggcggc tctagagcct ctgctaacca    1680
tgttcatgcc ttcttctttt tcctacagct cctgggcaac gtgctggttg ttgtgctgtc    1740
tcatcatttt ggcaaagaat tcgccaccat ggtgagcaag ggcgaggagc tgttcaccgg    1800
ggtggtgccc atcctggtcg agctggacgg cgacgtaaac ggccacaagt tcagcgtgtc    1860
cggcgagggc gagggcgatg ccacctacgg caagctgacc ctgaagttca tctgcaccac    1920
cggcaagctg cccgtgccct ggcccaccct cgtgaccacc ctgacctacg gcgtgcagtg    1980
cttcagccgc taccccgacc acatgaagca gcacgacttc ttcaagtccg ccatgcccga    2040
aggctacgtc caggagcgca ccatcttctt caaggacgac ggcaactaca agacccgcgc    2100
cgaggtgaag ttcgagggcg acaccctggt gaaccgcatc gagctgaagg gcatcgactt    2160
caaggaggac ggcaacatcc tggggcacaa gctggagtac aactacaaca gccacaacgt    2220
ctatatcatg gccgacaagc agaagaacgg catcaaggtg aacttcaaga tccgccacaa    2280
catcgaggac ggcagcgtgc agctcgccga ccactaccag cagaacaccc ccatcggcga    2340
cggccccgtg ctgctgcccg acaaccacta cctgagcacc cagtccgccc tgagcaaaga    2400
ccccaacgag aagcgcgatc acatggtcct gctggagttc gtgaccgccg ccgggatcac    2460
tctcggcatg gacgagctgt acaagtaaga attcactcct caggtgcagg ctgcctatca    2520
gaaggtggtg gctggtgtgg ccaatgccct ggctcacaaa taccactgag atcttttttcc    2580 ctctgccaaa aattatgggg acatcatgaa gccccttgag catctgactt ctggctaata    2640
aaggaaattt attttcattg caatagtgtg ttggaatttt ttgtgtctct cactcggaag    2700
gacatatggg agggcaaatc atttaaaaca tcagaatgag tatttggttt agagtttggc    2760
aacatatgcc atatgctggc tgccatgaac aaaggtggct ataaagaggt catcagtata    2820
tgaaacagcc ccctgctgtc cattccttat tccatagaaa agccttgact tgaggttaga    2880 tttttttat attttgtttt gtgttatttt tttctttaac atccctaaaa ttttccttac    2940
atgttttact agccagattt ttcctcctct cctgactact cccagtcata gctgtccctc    3000
ttctcttatg aagatccctc gacctgcagc ccaagctcgg ggccaggtcg ccgagcgat    3060 cgcgagaatt cggcttaagt gagtcgtatt acggactggc cgtcgtttta caacgtcgtg    3120
actgggaaaa ccctggcgtt acccaactta atcgccttgc agcacatccc cctttcgcca    3180
gctggcgtaa tagcgaagag gcccgcaccg atcgcccttc ccaacagttg cgcagcctga    3240
atggcgaatg gcgcttcgct tggtaataaa gcccgcttcg gcgggctttt ttttggttaa    3300
ctacgtcagg tggcactttt cggggaaatg tgcgcggaac ccctatttgt ttattttttct    3360 aaatacattc aaatatgtat ccgctcatga gacaataacc ctgataaatg cttcaataat    3420
attgaaaaag gaagagtatg agtattcaac atttccgtgt cgcccttatt cccttttttg    3480
cggcattttg ccttcctgtt tttgctcacc cagaaacgct ggtgaaagta aaagatgctg    3540
aagatcagtt gggtgcacga gtgggttaca tcgaactgga tctcaacagc ggtaagatcc    3600
ttgagagttt tcgccccgaa gaacgttctc caatgatgag cactttttaaa gttctgctat    3660 gtggcgcggt attatcccgt gttgacgccg ggcaagagca actcggtcgc cgcatacact    3720
attctcagaa tgacttggtt gagtactcac cagtcacaga aaagcatctt acggatggca    3780
```

-continued

```
tgacagtaag agaattatgc agtgctgcca taaccatgag tgataacact gcggccaact  3840
tacttctgac aacgatcgga ggaccgaagg agctaaccgc tttttttgcac aacatggggg  3900 atcatgtaac tcgccttgat cgttgggaac cggagctgaa tgaagccata ccaaacgacg  3960
agcgtgacac cacgatgcct gtagcaatgg caacaacgtt gcgcaaacta ttaactggcg  4020
aactacttac tctagcttcc cggcaacaat taatagactg gatggaggcg gataaagttg  4080
caggaccact tctgcgctcg gcccttccgg ctggctggtt tattgctgat aaatctggag  4140
ccggtgagcg tgggtctcgc ggtatcattg cagcactggg gccagatggt aagccctccc  4200
gtatcgtagt tatctacacg acggggagtc aggcaactat ggatgaacga atagacaga  4260 tcgctgagat aggtgcctca ctgattaagc attggtaact gtcagaccaa gtttactcat  4320
atatacttta gattgattta ccccggttga taatcagaaa agccccaaaa acaggaagat  4380
tgtataagca aatatttaaa ttgtaaacgt taatattttg ttaaaattcg cgttaaattt  4440
ttgttaaatc agctcatttt ttaaccaata ggccgaaatc ggcaaaatcc cttataaatc  4500
aaaagaatag cccgagatag ggttgagtgt tgttccagtt tggaacaaga gtccactatt  4560
aaagaacgtg gactccaacg tcaaagggcg aaaaaccgtc tatcagggcg atggcccact  4620
acgtgaacca tcacccaaat caagtttttt ggggtcgagg tgccgtaaag cactaaatcg  4680
gaaccctaaa gggagccccc gatttagagc ttgacgggga aagcgaacgt ggcgagaaag  4740
gaagggaaga aagcgaaagg agcgggcgct agggcgctgg caagtgtagc ggtcacgctg  4800
cgcgtaacca ccagcaccgc cgcgcttaat gcgccgctac agggcgcgta aaaggatcta  4860
ggtgaagatc cttttttgata atctcatgac caaaatcccct taacgtgagt tttcgttcca  4920
ctgagcgtca gacccccgtag aaaagatcaa aggatcttct tgagatcctt ttttttctgcg  4980 cgtaatctgc tgcttgcaaa caaaaaaacc accgctacca gcggtggttt gtttgccgga  5040
tcaagagcta ccaactcttt ttccgaaggt aactggcttc agcagagcgc agataccaaa  5100
tactgttctt ctagtgtagc cgtagttagg ccaccacttc aagaactctg tagcaccgcc  5160 tacataccctc gctctgctaa tcctgttacc agtggctgct gccagtggcg ataagtcgtg  5220
tcttaccggg ttggactcaa gacgatagtt accggataag gcgcagcggt cgggctgaac  5280
ggggggttcg tgcacacagc ccagcttgga gcgaacgacc tacaccgaac tgagatacct  5340
acagcgtgag ctatgagaaa gcgccacgct tcccgaaggg agaaaggcgg acaggtatcc  5400
ggtaagcggc agggtcggaa caggagagcg cacgagggag cttccagggg gaaacgcctg  5460
gtatctttat agtcctgtcg ggtttcgcca cctctgactt gagcgtcgat ttttgtgatg  5520
ctcgtcaggg gggcggagcc tatgaaaaa cgccagcaac gcggccttt tacggttcct  5580 ggccttttgc tggccttttg ctcacatgta atgtgagtta gctcactcat taggcacccc  5640
aggctttaca ctttatgctt ccggctcgta tgttgtgtgg aattgtgagc ggataacaat  5700
ttcacacagg aaacagctat gaccatgatt acgccaagct acgtaatacg actcactag  5759
```